US006797511B1

(12) United States Patent
Kosik et al.

(10) Patent No.: US 6,797,511 B1
(45) Date of Patent: Sep. 28, 2004

(54) ALARM RELATED PEPTIDES AND NUCLEIC ACIDS AND DIAGNOSIS USING THEM

(75) Inventors: Kenneth S. Kosik, Belmont, MA (US); Jianhua Zhou, Malden, MA (US)

(73) Assignee: Brigham and Women's Hospital, Boston, MA (US)

( * ) Notice: Subject to any disclaimer, the term of this patent is extended or adjusted under 35 U.S.C. 154(b) by 617 days.

(21) Appl. No.: 09/629,498

(22) Filed: Jul. 31, 2000

Related U.S. Application Data

(62) Division of application No. 08/982,785, filed on Dec. 2, 1997, now Pat. No. 6,258,929.
(60) Provisional application No. 60/031,556, filed on Dec. 2, 1996.
(51) Int. Cl.[7] .......................... C12N 15/63; C12N 5/00; C07H 21/02; C07H 21/04
(52) U.S. Cl. ..................... 435/320.1; 435/325; 536/23.5
(58) Field of Search ............................. 435/320.1, 325; 536/23.5

(56) References Cited

U.S. PATENT DOCUMENTS

| 5,470,966 A | 11/1995 | Hirano et al. |
| 5,986,054 A | 11/1999 | St. George-Hyslop et al. |

FOREIGN PATENT DOCUMENTS

| WO | WO 97/27296 | 7/1997 |
| WO | WO 98/01549 | 1/1998 |

OTHER PUBLICATIONS

Behrens et al., "Functional Interaction of β–catenin with the Transcription Factor LEF–1," *Nature*, 382:638–642, 1996.
Bhanot et al., "A New Member of the Frizzled Family from Drosophila Functions as a Wingless Receptor,"*Nature*, 382:225–230, 1996.
Daniel et al., The Tyrosine Kinase Substrate p120 $^{cas}$ Binds Directly to E–Cadherin But Not to the Adenomatous Polyposis Coli Protein or β–Catenin, *Molecular and Cellular Biology*, 15:4819–4824, 1995.
Dewji et al., "Genetic Clues to Alzheimer's Disease," *Science*, 271:159–161, 1996.
DiNardo et al., Two–tiered Regulation of Spatially Patterned Engrailed Gene Expression During Drosophila Embryogenesis, *Nature*, 332:604–609, 1988.
Grant et al., "The Caenorhabditis elegans sel–1 Gene, A Negative Regulator of Lin–12 and glp–1, Encodes A Predicted Extracellular Protein," *Genetics*, 143:237–247, 1996.
Guger et al., "β–Catenin Has Wnt–Like Activity and Mimics the Nieuwkoop Signaling Center in Xenopus Dorsal–Ventral Patterning," *Developmental Biology*, 172:115–125, 1995.
Hinck et al., "Wnt–1 Modulates Cell–Cell Adhesion in Mammalin Cells by Stabilizing β–Catenin Binding to the Cell Adhesion Protein Cadherin," *The Journal of Cell Biology*, 124:729–741, 1994.

Levitan et al., "Facilitation of Lin–12–mediated Signalling by sel–12, a Caenorhaditis Elegans S182 Alzheimer's Disease Gene," *Nature*, 377:351–354, 1995.
Levy–Lahad et al., "A Familial Alzheimer's Disease Locus on Chromosome I," *Science*, 269–970–973, 1995.
Levy–Lahad et al., "Candidate Gene for the Chromosome 1 Familial Alzheimer's Disease Locus," *Science*, 269:973–977, 1995.
Martinez Arias et al., Role of Segment Polarity Genes in the Definition and Maintenance of Cell States in the Drosophila Embryo, *Development*, 103:157–170, 1988.
Mattson et al., "Cell and Molecular Neurobiology of Presenilins: A Role for the Endoplasmic Reticulum in the Pathogenesis of Alzheimer's Disease?", *Journal of Neuroscience Research*, 50:505–513, 1997.
McCrea et al., "A Homolog of the Armadillo Protein in Drosophila (Plakoglobin) Associated with E–Cadherin,"*Science*, 254:1359–1361, 1991.
Peifer et al., "The Vertebrate Adhesive Junction Proteins β–catenin and Plakoglobin and the Drosophila Segment Polarity Gene Armadillo Form a Multigene Family with Similar Properties,"*The Journal of Cell Biology*, 118:681–692, 1992.
Reynolds et al., "p120, A Novel Substrate of Protein Tyrosine Kinase Receptors and of p60$^{v-src}$ is Related to Cadherin–binding Factors β–catenin, Plakoglobin and Armadillo," *Oncogene*, 7:2439–2445, 1992.
Riggleman et al., "Molecular Analysis of the Armadillo Locus: Uniformly Distributed Transcripts and a Protein with Novel Internal Repeats are Associated with a Drosophila Segment Polarity Gene," *Genes & Development*, 3:96–113, 1989.
Riggleman et al., "Spatial Expression of the Drosophila Segment Polarity gene Armadillo is Posttranscriptionally Regulated by Wingless," *Cell*, 63:549–560, 1990.
Rogaev et al., "Familial Alzheimer's Disease in Kindreds with Missense Mutations in a Gene on Chromosome 1 Related to the Alzheimer's Disease Type 3 Gene," *Nature*, 376:775–778, 1995.
Rubinfeld et al., "The APC Protein and E–cadherin Form Similar but Independent Complexes with α–Catenin, 62–Catenin, and Plakoglobin," *The Journal of Biological Chemistry*, 270:5549–5555, 1995.
Selkoe, "Cell Biology of the Amyloid β–Protein Precursor and the Mechanism of Alzheimer's Disease," *Annual Review of Cell Biology*, 10:373–403, 1994.

(List continued on next page.)

*Primary Examiner*—Gary Kunz
*Assistant Examiner*—Stephen Gucker
(74) *Attorney, Agent, or Firm*—Fish & Richardson, P.C.

(57) ABSTRACT

We have identified a novel protein, named ALARM or δ-catenin, on the basis of its ability to bind to presenilin 1. ALARM contains 4 copies of the arm repeat and is expressed almost exclusively in brain tissue.

11 Claims, 8 Drawing Sheets

OTHER PUBLICATIONS

Sherrington et al., "Cloning of a Gene Bearing Missense Mutations in Early–onset Familial Alzheimer's Disease," *Nature*, 375:754–760, 1995.

Shibamoto et al., "Association of p120, a Tyrosine Kinase Substrate, with E–Cadherin/Catenin Complexes," *The Journal of Cell Biology*, 128:949–957, 1995.

Staddon et al., "p120, a p120–Related Protein (p100), and the Cadherin/Catenin Complex," *The Journal of Cell Biology*, 130:369–381, 1995.

Sundaram et al., "Suppressors of a line–12 Hypomorph Define Genes That Interact With Both lin–12 and glp–1 in Caenorhabditis Elegans," *Genetics*, 135:765–783, 1993.

Tao et al., "β–Catenin Associates with the Actin–bundling Protein Fascin in a Noncadherin Complex," *The Journal of Cell Biology*, 134:1271–1281, 1996.

Xia et al., "Interaction Between Amyloid Precursor Protein and Presenilins in Mammalian Cells: Implications for the Pathogenesis of Alzheimer Disease," *Proc. Natl. Acad. Sci. USA*, 94:8208–8213, 1997.

Yochem et al., "The Caenorhabditis Elegans Lin–12 Gene Encodes a Transmembrane Protein with Overall Similarity to Drosophila Notch," *Nature*, 335:547–550, 1988.

Zhou et al., "Presenilin 1 Interaction in the Brain with a Novel Member of the Armadillo Family," *NeuroReport*, 8:1489–1494, 1997.

Zhou et al., "Presenilin 1 Interaction in the Brain with a Novel Member of the Armadillo Family," *NeuroReport*, 8:2085–2090, 1997.

```
        GCACCAGCTCGCCCATCAACATCGTCGTGTCCTCGGCCGGCCTGTCCCCGATCCGCGTGA
    1   ------------+---------+---------+---------+---------+---------+   60
        CGTGGTCGAGCGGGTAGTTGTAGCAGCACAGGAGCCGGCCGGACAGGGGCTAGGCGCACT c

CCTCGCCCCCACCGTGCAGTCCACCATCTCCTCCTCGCCCATCCACCAGCTGAGCTCCA
   61   ------------+---------+---------+---------+---------+---------+  120
        GGAGCGGGGGGTGGCACGTCAGGTGGTAGAGGAGGAGCGGGTAGGTGGTCGACTCGAGGT

CCATCGGCACGTACGCCACCCTGTCGCCCACCAAGCGCCTGGTCCACGCGTCCGAGCAGT
  121   ------------+---------+---------+---------+---------+---------+  180
        GGTAGCCGTGCATGCGGTGGGACAGCGGGTGGTTCGCGGACCAGGTGCGCAGGCTCGTCA c

ACAGCAAGCACTCGCAGGAGCTGTATGCCACGGCCACCCTCCAGAGGCCGGGCAGCCTGG
  181   ------------+---------+---------+---------+---------+---------+  240
        TGTCGTTCGTGAGCGTCCTCGACATACGGTGCCGGTGGGAGGTCTCCGGCCCGTCGGACC

CAGCTGGTTCCCGAGCCTCATACAGCAGCCAGCATGGGCACCTGGGCCCAGAGTTGCGGG
  241   ------------+---------+---------+---------+---------+---------+  300
        GTCGACCAAGGGCTCGGAGTATGTCGTCGGTCGTACCCGTGGACCCGGGTCTCAACGCCC

CCCTGCAGTCCCCAGAACACCACATAGATCCCATCTATGAAGTCCGCGTCTATCAGAAGC
  301   ------------+---------+---------+---------+---------+---------+  360
        GGGACGTCAGGGGTCTTGTGGTGTATCTAGGGTAGATACTTCAGGCGCAGATAGTCTTCG

CCCCTATGAGGAGTCTCAGCCAGAGCCAGGGGGTCCCTCTGCCGCCAGCACACACCGGCA
  361   ------------+---------+---------+---------+---------+---------+  420
        GGGGATACTCCTCAGAGTCGGTCTCGGTCCCCCAGGGAGACGGCGGTCGTGTGTGGCCGT
              M   R   S   L   S   Q   S   Q   G   V   P   L   P   P   A   H   T   G   T   -

CCTACCGCACGAGCACAGCCCCATCTTCCCCTGGTGTCGACTCCGTCCCCTTGCAGCGCA
  421   ------------+---------+---------+---------+---------+---------+  480
        GGATGGCGTGCTCGTGTCGGGGTAGAAGGGGACCACAGCTGAGGCAGGGGAACGTCGCGT c             Y   R   T   S   T   A   P   S   S   P   G   V   D   S   V   P   L   Q   R   T   -

CAGGCAGCCAGCACGGCCCACAGAATGCCGCCGCGGCCACCTTCCAGAGGGCCAGCTATG
  481   ------------+---------+---------+---------+---------+---------+  540
        GTCCGTCGGTCGTGCCGGGTGTCTTACGGCGGCGCCGGTGGAAGGTCTCCCGGTCGATAC c             G   S   Q   H   G   P   Q   N   A   A   A   A   T   F   Q   R   A   S   Y   A   -

CCGCCGGCCCAGCCTCCAATTACGCGGACCCCTACCGACAGCTGCAGTATTGTCCCTCTG
  541   ------------+---------+---------+---------+---------+---------+  600
        GGCGGCCGGGTCGGAGGTTAATGCGCCTGGGGATGGCTGTCGACGTCATAACAGGGAGAC c             A   G   P   A   S   N   Y   A   D   P   Y   R   Q   L   Q   Y   C   P   S   V   -
```

FIG. 1A

```
        TTGAGTCTCCATACAGCAAATCCGGCCCTGCTCTCCCGCCTGAAGGCACCTTGGCCAGGT
   601  ------------+---------+---------+---------+---------+---------+  660
        AACTCAGAGGTATGTCGTTTAGGCCGGGACGAGAGGGCGGACTTCCGTGGAACCGGTCCA c         E  S  P  Y  S  K  S  G  P  A  L  P  P  E  G  T  L  A  R  S -

CCCCGTCCATTGATAGCATTCAGAAAGATCCCAGAGAATTTGGATGGAGAGACCCGGAAC
   661  ------------+---------+---------+---------+---------+---------+  720
        GGGGCAGGTAACTATCGTAAGTCTTTCTAGGGTCTCTTAAACCTACCTCTCTGGGCCTTG c         P  S  I  D  S  I  Q  K  D  P  R  E  F  G  W  R  D  P  E  L -

TGCCGGAAGTGATTCAGATGTTGCAGCACCAGTTTCCCTCGGTCCAGTCTAACGCGGCAG
   721  ------------+---------+---------+---------+---------+---------+  780
        ACGGCCTTCACTAAGTCTACAACGTCGTGGTCAAAGGGAGCCAGGTCAGATTGCGCCGTC c         P  E  V  I  Q  M  L  Q  H  Q  F  P  S  V  Q  S  N  A  A  A -

CCTACTTGCAACACCTCTGTTTTGGAGACAACAAAATTAAAGCCGAGATAAGGAGACAAG
   781  ------------+---------+---------+---------+---------+---------+  840
        GGATGAACGTTGTGGAGACAAAACCTCTGTTGTTTTAATTTCGGCTCTATTCCTCTGTTC c         Y  L  Q  H  L  C  F  G  D  N  K  I  K  A  E  I  R  R  Q  G -

GAGGCATCCAGCTCCTGGTGGACCTGTTGGATCATCGGATGACCGAAGTCCACCGTAGTG
   841  ------------+---------+---------+---------+---------+---------+  900
        CTCCGTAGGTCGAGGACCACCTGGACAACCTAGTAGCCTACTGGCTTCAGGTGGCATCAC c         G  I  Q  L  L  V  D  L  L  D  H  R  M  T  E  V  H  R  S  A -

CCTGTGGAGCTCTGAGAAACCTGGTGTATGGGAAGGCCAACGATGATAACAAAATTGCCC
   901  ------------+---------+---------+---------+---------+---------+  960
        GGACACCTCGAGACTCTTTGGACCACATACCCTTCCGGTTGCTACTATTGTTTTAACGGG c         C  G  A  L  R  N  L  V  Y  G  K  A  N  D  D  N  K  I  A  L -

TGAAAAACTGTGGTGGCATCCCAGCACTGGTGAGGTTACTCCGCAAGACGACTGACCTGG
   961  ------------+---------+---------+---------+---------+---------+ 1020
        ACTTTTTGACACCACCGTAGGGTCGTGACCACTCCAATGAGGCGTTCTGCTGACTGGACC c         K  N  C  G  G  I  P  A  L  V  R  L  L  R  K  T  T  D  L  E -

AGATCCGGGAGCTGGTCACAGGAGTCCTTTGGAACCTCTCCTCATGCGATGCACTCAAAA
  1021  ------------+---------+---------+---------+---------+---------+ 1080
        TCTAGGCCCTCGACCAGTGTCCTCAGGAAACCTTGGAGAGGAGTACGCTACGTGAGTTTT c         I  R  E  L  V  T  G  V  L  W  N  L  S  S  C  D  A  L  K  M -

TGCCAATCATCCAGGATGCCCTAGCAGTACTGACCAACGCGGTGATTATCCCCCACTCAG
  1081  ------------+---------+---------+---------+---------+---------+ 1140
        ACGGTTAGTAGGTCCTACGGGATCGTCATGACTGGTTGCGCCACTAATAGGGGGTGAGTC c         P  I  I  Q  D  A  L  A  V  L  T  N  A  V  I  I  P  H  S  G -

GCTGGGAAAATTCGCCTCTTCAGGATGATCGGAAAATACAGCTGCATTCATCACAGGTGC
  1141  ------------+---------+---------+---------+---------+---------+ 1200
        CGACCCTTTTAAGCGGAGAAGTCCTACTAGCCTTTTATGTCGACGTAAGTAGTGTCCACG c         W  E  N  S  P  L  Q  D  D  R  K  I  Q  L  H  S  S  Q  V  L -

TGCGTAACGCCACCGGGTGCTTAAGGAATGTTAGTTCGCCCGGAGAGGAGGCCCGCAGAA
  1201  ------------+---------+---------+---------+---------+---------+ 1260
        ACGCATTGCGGTGGCCCACGAATTCCTTACAATCAAGCGGGCCTCTCCTCCGGGCGTCTT
```

FIG. 1B

```
c       R  N  A  T  G  C  L  R  N  V  S  S  P  G  E  E  A  R  R  R  -
        GGATGAGAGAGTGTGATGGGCTTACGGATGCCTTGCTGTACGTGATCCAGTCTGCGCTGG
1261    ------------+----------+----------+----------+----------+----------+   1320
        CCTACTCTCTCACACTACCCGAATGCCTACGGAACGACATGCACTAGGTCAGACGCGACC c       M  R  E  C  D  G  L  T  D  A  L  L  Y  V  I  Q  S  A  L  G  -
        GGAGCAGTGAGATCGATAGCAAGACCGTTGAAAACTGTGTGTGCATTTTAAGGAACCTCT
1321    ------------+----------+----------+----------+----------+----------+   1380
        CCTCGTCACTCTAGCTATCGTTCTGGCAACTTTTGACACACACGTAAAATTCCTTGGAGA c       S  S  E  I  D  S  K  T  V  E  N  C  V  C  I  L  R  N  L  S  -
        CGTACCGGCTGGCGGCAGAAACGTCTCAGGGACAGCACATGGGCACGGACGAGCTGGACG
1381    ------------+----------+----------+----------+----------+----------+   1440
        GCATGGCCGACCGCCGTCTTTGCAGAGTCCCTGTCGTGTACCCGTGCCTGCTCGACCTGC c       Y  R  L  A  A  E  T  S  Q  G  Q  H  M  G  T  D  E  L  D  G  -
        GGCTACTCTGTGGCGAGGCCAATGGCAAGGATGCTGAGAGCTCTGGGTGCTGGGGCAAGA
1441    ------------+----------+----------+----------+----------+----------+   1500
        CCGATGAGACACCGCTCCGGTTACCGTTCCTACGACTCTCGAGACCCACGACCCCGTTCT c       L  L  C  G  E  A  N  G  K  D  A  E  S  S  G  C  W  G  K  K  -
        AGAAGAAGAAAAAGAAATCCCAAGATCAGTGGGATGGAGTAGGACCTCTTCCAGACTGTG
1501    ------------+----------+----------+----------+----------+----------+   1560
        TCTTCTTCTTTTTCTTTAGGGTTCTAGTCACCCTACCTCATCCTGGAGAAGGTCTGACAC c       K  K  K  K  S  Q  D  Q  W  D  G  V  G  P  L  P  D  C  A  -
        CTGAACCACCAAAAGGGATCCAGATGCTGTGGCACCCATCAATAGTCAAACCCTACCTCA
1561    ------------+----------+----------+----------+----------+----------+   1620
        GACTTGGTGGTTTTCCCTAGGTCTACGACACCGTGGGTAGTTATCAGTTTGGGATGGAGT c       E  P  P  K  G  I  Q  M  L  W  H  P  S  I  V  K  P  Y  L  T  -
        CACTGCTCTCTGAGTGCTCAAATCCAGACACGCTGGAAGGGGCGGCAGGCGCCCTGCAGA
1621    ------------+----------+----------+----------+----------+----------+   1680
        GTGACGAGAGACTCACGAGTTTAGGTCTGTGCGACCTTCCCCGCCGTCCGCGGGACGTCT c       L  L  S  E  C  S  N  P  D  T  L  E  G  A  A  G  A  L  Q  N  -
        ACTTGGCTGCAGGGAGCTGGAAGTGGTCAGTATATATCCGAGCCGCTGTCCGAAAAGAGA
1681    ------------+----------+----------+----------+----------+----------+   1740
        TGAACCGACGTCCCTCGACCTTCACCAGTCATATATAGGCTCGGCGACAGGCTTTTCTCT c       L  A  A  G  S  W  K  W  S  V  Y  I  R  A  A  V  R  K  E  K  -
        AAGGCCGGCCCATCCTCGTGGAGCTGCTCCGAATAGACAATGACCGTGTGGCGTGCGCGG
1741    ------------+----------+----------+----------+----------+----------+   1800
        TTCCGGCCGGGTAGGAGCACCTCGACGAGGCTTATCTGTTACTGGCACACCGCACGCGCC c       G  R  P  I  L  V  E  L  L  R  I  D  N  D  R  V  A  C  A  V  -
        TGGCCACTGCGCTGCGGAACATGGCCTTGGACGTCAGAAATAAGGAGCTCATCGGCAAAT
1801    ------------+----------+----------+----------+----------+----------+   1860
        ACCGGTGACGCGACGCCTTGTACCGGAACCTGCAGTCTTTATTCCTCGAGTAGCCGTTTA c       A  T  A  L  R  N  M  A  L  D  V  R  N  K  E  L  I  G  K  Y  -
        ACGCCATGCGAGACCTAGTCCACAGGCTTCCAGGAGGGAACAACAGCAACAACACTGCAA
1861    ------------+----------+----------+----------+----------+----------+   1920
```

FIG. 1C

```
            TGCGGTACGCTCTGGATCAGGTGTCCGAAGGTCCTCCCTTGTTGTCGTTGTTGTGACGTT
   c        A  M  R  D  L  V  H  R  L  P  G  G  N  S  N  N  T  A  S  -

GCAAGGCCATGTCGGATGACACAGTGACAGCTGTCTGCTGCACACTGCACGAAGTGATTA
   1921     --------+---------+---------+---------+---------+---------+  1980
            CGTTCCGGTACAGCCTACTGTGTCACTGTCGACAGACGACGTGTGACGTGCTTCACTAAT c        K  A  M  S  D  D  T  V  T  A  V  C  C  T  L  H  E  V  I  T  -

CCAAGAACATGGAGAACGCCAAGGCCTTACGGGATGCCGGTGGCATCGAGAAGTTGGTCG
   1981     --------+---------+---------+---------+---------+---------+  2040
            GGTTCTTGTACCTCTTGCGGTTCCGGAATGCCCTACGGCCACCGTAGCTCTTCAACCAGC c        K  N  M  E  N  A  K  A  L  R  D  A  G  G  I  E  K  L  V  G  -

GCATCTCCAAAAGCAAAGGAGATAAACACTCTCCAAAAGTGGTCAAGGCTGCATCTCAGG
   2041     --------+---------+---------+---------+---------+---------+  2100
            CGTAGAGGTTTTCGTTTCCTCTATTTGTGAGAGGTTTTCACCAGTTCCGACGTAGAGTCC c        I  S  K  S  K  G  D  K  H  S  P  K  V  V  K  A  A  S  Q  V  -

TCCTCAACAGCATGTGGCAGTACCGAGATCTGAGGAGTCTCTACAAAAAGGATGGATGGT
   2101     --------+---------+---------+---------+---------+---------+  2160
            AGGAGTTGTCGTACACCGTCATGGCTCTAGACTCCTCAGAGATGTTTTTCCTACCTACCA c        L  N  S  M  W  Q  Y  R  D  L  R  S  L  Y  K  K  D  G  W  S  -

CACAATACCACTTTGTAGCCTCGTCTTCAACCATCGAGAGGGACCGGCAAAGGCCCTACT
   2161     --------+---------+---------+---------+---------+---------+  2220
            GTGTTATGGTGAAACATCGGAGCAGAAGTTGGTAGCTCTCCCTGGCCGTTTCCGGGATGA c        Q  Y  H  F  V  A  S  S  S  T  I  E  R  D  R  Q  R  P  Y  S  -

CCTCCTCCCGCACGCCCTCCATCTCCCCTGTGCGCGTGTCTCCCAACAACCGCTCAGCAA
   2221     --------+---------+---------+---------+---------+---------+  2280
            GGAGGAGGGCGTGCGGGAGGTAGAGGGGACACGCGCACAGAGGGTTGTTGGCGAGTCGTT c        S  S  R  T  P  S  I  S  P  V  R  V  S  P  N  N  R  S  A  S  -

GTGCCCCAGCTTCACCTCGGGAAATGATCAGCCTCAAAGAAAGGAAAACAGACTACGAGT
   2281     --------+---------+---------+---------+---------+---------+  2340
            CACGGGGTCGAAGTGGAGCCCTTTACTAGTCGGAGTTTCTTTCCTTTTGTCTGATGCTCA c        A  P  A  S  P  R  E  M  I  S  L  K  E  R  K  T  D  Y  E  C  -

GCACCGGCAGCAACGCCACCTACCACGGAGCTAAAGGCGAACACACTTCCAGGAAAGATG
   2341     --------+---------+---------+---------+---------+---------+  2400
            CGTGGCCGTCGTTGCGGTGGATGGTGCCTCGATTTCCGCTTGTGTGAAGGTCCTTTCTAC c        T  G  S  N  A  T  Y  H  G  A  K  G  E  H  T  S  R  K  D  A  -

CCATGACAGCTCAAAACACTGGAATTTCAACTTTGTATAGGAATTCTACAAGAAATTACG
   2401     --------+---------+---------+---------+---------+---------+  2460
            GGTACTGTCGAGTTTTGTGACCTTAAAGTTGAAACATATCCTTAAGATGTTCTTTAATGC c        M  T  A  Q  N  T  G  I  S  T  L  Y  R  N  S  T  R  N  Y  D  -

ATGAGTCCTTCTTCGAGGACCAGGTCCACCATCGCCCTCCCGCCAGCGAGTACACCATGC
   2461     --------+---------+---------+---------+---------+---------+  2520
            TACTCAGGAAGAAGCTCCTGGTCCAGGTGGTAGCGGGAGGGCGGTCGCTCATGTGGTACG c        E  S  F  F  E  D  Q  V  H  H  R  P  P  A  S  E  Y  T  M  H  -
```

FIG. 1D

```
        ACCTGGGTCTCAAGTCCACCGGCAACTACGTTGACTTCTACTCAGCTGCCCGTCCCTACA
2521    ------------+----------+----------+----------+----------+    2580
        TGGACCCAGAGTTCAGGTGGCCGTTGATGCAACTGAAGATGAGTCGACGGGCAGGGATGT c       L  G  L  K  S  T  G  N  Y  V  D  F  Y  S  A  A  R  P  Y  S -

GTGAACTGAACTATGAAACGAGCCACTACCCGGCCTCCCCCGACTCCTGGGTGTGAGGAG
2581    ------------+----------+----------+----------+----------+    2640
        CACTTGACTTGATACTTTGCTCGGTGATGGGCCGGAGGGGGCTGAGGACCCACACTCCTC c       E  L  N  Y  E  T  S  H  Y  P  A  S  P  D  S  W  V  *

CAGGGCACAGGCGCTCCGGGAACAGTGCATGTGCATGCATACCACAAGACATTTCTTTCT
2641    ------------+----------+----------+----------+----------+    2700
        GTCCCGTGTCCGCGAGGCCCTTGTCACGTACACGTACGTATGGTGTTCTGTAAAGAAAGA

GTTTTGTTTTTTTCTCCTGCAAATTTAGTTTGTTAAAGCCTGTTCCATAGGAAGGCTGTG
2701    ------------+----------+----------+----------+----------+    2760
        CAAAACAAAAAAAGAGGACGTTTAAATCAAACAATTTCGGACAAGGTATCCTTCCGACAC

ATAACCAGTAAGGAAATATTAAGAGCTATTTTAGAAAGCTAAATGAATCGCAAGTTTAAC
2761    ------------+----------+----------+----------+----------+    2820
        TATTGGTCATTCCTTTATAATTCTCGATAAAATCTTTCGATTTACTTAGCGTTCAAATTG c       N  Q  *  G  N  I  K  S  Y  F  R  K  L  N  E  S  Q  V  * L -

TTGGAAATCAGTAGAAAGCTAAAGTGATCCTAAATATGACAGTGGGCAGCACCTTTCTAG
2821    ------------+----------+----------+----------+----------+    2880
        AACCTTTAGTCATCTTTCGATTTCACTAGGATTTATACTGTCACCCGTCGTGGAAAGATC

CGTGAGCTGTAAAGTAACGANAAGTGCTTTATACTGAACGTNGTTGATGGGAGGANANAC
2881    ------------+----------+----------+----------+----------+    2940
        GCACTCGACATTTCATTGCTNTTCACGAAATATGACTTGCANCAACTACCCTCCTNTNTG

AAGCATTCCGGCCGGTGGGGCNTANGGTTNTCNTTAACACAAT
2941    ------------+----------+----------+-----     2983
        TTCGTAAGGCCGGCCACCCCGNATNCCAANAGNAATTGTGTTA
```

FIG. 1E

Homology to repeated regions in armadillo, γ-catenin and β-catenin

```
armadillo   G G I P A L V R L L * * N * - D * * * L L * A A * G V L R N L S * * * * - - N K A I * * *
                        V Q E       K       R       S             A T           V                 S K L A
                                            S                                   H A i:          G G I Q L L V D L L - D H R - N T E - Y H R S A C G A L R N L V Y G K A N D D N L K I A L K N C
ii:         G G I P A L V R L L - R K T T D L E I R E L V T - G V L W N L S S C D A I - - L K M P I I Q
iii:        S I V K P Y L T L L - S E C S N P D T L E G A A - G A L Q N L A A G S - - - - W K W S V Y
iv:         K G R P I L V E L L - R I D N D R V - A C - A V A T A L R N H A L D V R - - - N K E L I G K Y
```

Homologous to consensus sequences:

i: 67%
ii: 70%
iii: 31%
iv: 59%

*: non-consensus sequence
-: gap

This alignment is essentially similar to that in a paper published in Oncogene (1992), 7: 2439-2445

FIG. 2

```
ALARM        5 SQSQGVPLPPAHTGTYRTSTAPSSPGV..........DSVPLQRTGSQH  43
               | |.....:..  ..   .  |||..:|          .||.|:|   .:.
pp120      230 SLSRVTRIEERYRPSMQVRVGGSSVDLHRFHPQVRVGGSSVDLHRFHPEP 279

44 GPQNAAAATFQRASYAAGPASNYA.........DPYRQLQYCPSVES...  81
               . :...  .:.  ....   |    |:|:         || |.|. :..: :
           280 YGLEDDQRSMGYDDLDYGMMSDYGTARRTGTPSDPRRRLRSTEDMIGEEV 329

82 ...PYSKSGPALPPEGTLARSPSIDSIQKD.PREFGWRDPELPEVIQMLQ 127
                  .|  ....|   |  .. |.||    |:||:.|:  |...  .||:|||||||.||.
           330 PPDQYYWAPLAQHERGSLA...SLDSLRKGMPPPSNWRQPELPEVIAMLG 376

128 HQFPSVQSNAAAYLQHLCFGDNKIKAEIRRQGGIQLLVDLLDHRMTEVHR 177
               .:...|.|||||||||||||:  ::|:|.:: :    ||.:||:||||...|||
           377 FRLDAVKSNAAAYLQHLCYRNDKVKTDVAKLKGIPILVGLLDHPKKEVHL 426

178 SACGALRNLVYGKANDDNKIALKNCGGIPALVRLLRKTTDLEIRELVTGV 227
               :|||||||:|: :|: ::|||||:|||:|:||||||||.  |::: |::||.
           427 GACGALKNISFGR.DQDNKIAIKNCDGVPALVRLLRKARDMDLTEVITGT 475

228 LWNLSSCDALKMPIIQDALAVLTNAVIIPHSGWENSPLQDDRKIQLHSSQ 277
               ||||||  |.:||.|::.||  .||:.|||||||||||..|  :|  :.  ::...
           476 LWNLSSHDSIKMEIVDHALHALTDEVIIPHSGWEREPNEDCKPRHIEWES 525

278 VLRNATGCLRNVSSPGEEARRRMRECDGLTDALLYVIQSALGSSEIDSKT 327
               ||  |..:||||||||.  .||||::|||||||.|||:::::|...:|  .:  |||
           526 VLTNTAGCLRNVSSERSEARRKLRECDGLVDALIFIVQAEIGQKDSDSKL 575

328 VENCVCILRNLSYRLAAETSQGQHMGTDELDGLLCGEANGKDAESSGCWG 377
               ||||||:|||||| .:   |..|::: :       .:: |..  ||..::....:|:|
           576 VENCVCLLRNLSYQVHREIPQAER.....YQEALPTVANSTGPHAASCFG 620

378 KK..KKKKKSQDQWDGVGPLPDCAEPPKGIQMLWHPSIVKPYLTLLSECS 425
               |    |   ||..:|.  ::....:|.   ..|::|.::|:|.:|: |:.||.|:..
           621 AKKGKGKKPTEDPANDTVDFPKRTSPARGYELLFQPEVVRIYISLLKESN 670

426 NPDTLEGAAGALQNLAAGSWKWSVYIRAAVRKEKGRPILVELLRIDNDRV 475
               .|..||:.|||:|||.||.|.|.|.|.:::   |||.|:|.||| .    .||| :::||
           671 TPAILEASAGAIQNLCAGRWTYGRYIRSALRQEKALSARAELLTSQHERV 720

476 ACAVATALRNMALDVRNKELIGKYAMRDLVHRLPGGNNSNNTASKAMSDD 525
               .  |....||||:|:|.|.|||||||||.|...:||..||||...    .|...:|:|
           721 VKAASGALRNLAVDARNKELIGKHARPNLVKNLPGGQQN...SSWNFSED 767

526 TVTAVCCTLHEVITKNMENAKALRDAGGIEKLVGISKGDKHSPKVVKA 575
               ||..:  |::|||..:|:|.||  ||:...|||||| |.||   :..|.|  |:|
           768 TVVSILNTINEVIAENLEAAKKLRETQGIEKLVLINKS..GNRSEKEVRA 815

576 ASQVLNSMWQYRDLRSLYKKDGWSQYHF.VASSSTIERDRQRPYSSSRTP 624
               |.  ||...:|.|:||..  ..|:||..   .|   |.  ...  .:.  :.|..|   |
           816 AALVLQTIWGYKELRKPLEKEGWKKSDFQVNLNNASRSQSSHSYDDSTLP 865

625 SISPVRVSPNNRSASAPASPREMISLKERKTDYECTGSNATYHGAKGEHT 674
               |...  .  |.||  |.  |       |.||  ..  .:..  |  |: .
           866 LIDRNQKSDNNYST...........LNERGDHNRTLDRS....GDLGDME 900

675 SRKDAMTAQNTGISTL 690
               . |:| |.      :
           901 PLKGAPLMQK.....I 912
```

FIG. 3

```
ALARM    ------    2  RSLSQSQGVPLPPAHTGTYRTSTAPSSP................GVD       32
                      ..||:|.  .:  .: .:.|. :|...|.                  .:.
γ-catenin --       60 STLSMSNRGSMYDGLADNYNYGTTSKSSYYSKFQAGNGSWGYPIYNGTLK 109

33 SVDLQRTCSQHCIQNAAAATFQRACYAAGPACNYADPYRQLQYCPSVESP  82
                      . | .|  | ..:  :..  :.|:|:....|:.     ...:. :.| ..
                  110 REPDNRRFSSYSQMENWRRHYPRGSCNTTGAGSDICFMQKIKASRSIDDL 159

83 YSKSGPALPPEGTLA...........................RSPSIDS 104
                      |:.. ...|  ..|||:                          |.||..|
                  160 YCDPRGTL.RKGTLGSKGQKTTQMRYSFYSTCSGQKAIKKCPVRPPSCAS 208

105 IQKDF........REFGW...............RDPELPEVIQMLQMQF 130
                      |...         ::::              .: .:|...:| | |
                  209 KQDPVYIPPISCNKDLSFGWSRASSKICSEDIECSCLTIPKAVQYLEEQD 250

131 PSVQSNAAAYLQHLCFGDNKIKAEIRRQGGIQLLVDLLDHRMTRVHRSAC 180
                      .. |. :| |:|| ||.|:. |..:  .  |||   |||||  . :|...|.
                  259 EKYQAIGAYYIQHTCFQDESAKQQVYQLGGICKLVDLLRSPNQNVQQAAA 308

181 GALRNLVYGKANDDNKIALKNCGGIPALVRLLRKTTDDEIRELVTGVLWN 230
                      ||||||||:  .. .|||.. |.|||||.|  ||.. :||:|||
                  309 CALRNLVFRET..TNKLETRRQNGIREAVELLRRTGNAEIQKQLTGLLWN 356

231 LSSCDALKMPTTQDALAVLTNAVIIPHSGWENSPLQDDRKIQLHSSQVLR 280
                      |||.|.||  .:|.|||:||.:  ||||  |||  ::  ...:.  ::  ...:|:
                  357 LSSTDELKEELIADALPVLADRVIIPFSGWCDG..NSNMSREVVDPEVFF 404

281 NATGCLRNVSSPGEEARRRMRECDGLTDALLYVIQSALGSSEIDSKTVEN 330
                      |||||||||:||   ::..:|.  ||:..:||.|.|.|:   :|..::.|  .|.|.|||
                  405 NATGCLRNLSS.ADAGRQTMRNYSGLIDSLMAYVQMCVAASRCDDKSVEN 453

331 CVCILRNLSYRLAAETSQGQHMGTDELDGLLCCEANC.FDAESSCCWCKK 379
                      |:|:|:|||||||.||..     . .| |..  |: .:  .|.|||..|
                  454 CMCVLHNLSYRLDAEVP.......TRYRQLEYNARNAYTEKSSTGCESNK 496

380 KKKKKSQNQWDGVGPLPDCAEPPKGIQMLWHPSIVKPYLTLLSECSNPDT 429
                      ..|..  .:.:|   .|||:  ..  |||  .  |:|..  ::.||.|::.:....|
                  497 SDKMM.NNNYD..CPLPEEEINPKGSGWLYHSDAIRTYLNLMGKSKKDAT 543

430 LECAACALQNLAAC.EWKWEVYIRAAVRKEKGRPILVELLRIDNDRVACA 478
                      ||:.|||||||.|: ::...|.  .  .  ||||  |  :. ||. :|. |..
                  544 LEACAGALQNTTASKGLMSSGMSQLIGLKEKGLPQIARLLQSGNSDVVRS 593

479 VATALRNMALDVRNKELIGKYAMRDLVHRLPGGNNSNNTASKAMSDDTVT 528
                      .|. |.||. ...  . ::|. ..:..:  |..    :||.... |:|..
                  594 GASLLSNMSKKPLLMKVMGNQVFPEVTRLLTS.....HTGNTSNSEDILS 638

529 AVCCTLHEVITKNMENAKALRDAGGIEKLVGISKSKGDKHSPKVVRAASQ 578
                      ..|:|:::::::... :  ||..  ...:  ::.::.::::|.:    |||...||.
                  639 SACYTVRNLMASQPQLAKQYFSSSMLNNIINLCRSSA...SPKAAEAARL 685

579 VLNSMWQYRDLRSLYKKDGWSQYHFVASSSTIERDRQRPYRRR       621
                      :|..||  ::|.:..:..::|:..  :...   :. | :.|.
                  686 LLSDMWSSKELQGVLRQQGFDRNMLGTLAGA...NSLRNPTSR       725
```

ALARM RELATED PEPTIDES AND NUCLEIC ACIDS AND DIAGNOSIS USING THEM

CROSS REFERENCE TO RELATED APPLICATION

This application is a divisional (and claims the benefit of priority under 35 USC 120) of U.S. application Ser. No. 08/982,785, filed Dec. 2, 1997, now U.S. Pat. No. 6,258,929 which claims priority from U.S. Provisional Application Serial No. 60/031,556, filed Dec.2, 1996. The disclosures of the prior applications are considered part of (and are incorporated by reference in) the disclosure of this application.

STATEMENT AS TO FEDERALLY SPONSORED RESEARCH

This invention was made with Government support under AG06601 awarded by the National Institutes of Health. The Government has certain rights in the invention.

BACKGROUND OF THE INVENTION

The invention is in the general field of proteins involved in Alzheimer's disease.

Various genes and gene products involved in the development of Alzheimer's disease have been identified. Neuritic plaques characteristic of the disease are composed of β-amyloid (Aβ), which are oligopeptides of about 40–43 amino acids in length derived from the β-amyloid precursor protein (βAPP). Mutations in the gene encoding βAPP are associated with some cases of familial Alzheimer's disease. Other cases of familial Alzheimer's disease have been associated with mutations in two other loci, presenilin-1 and presinilin-2.

SUMMARY OF THE INVENTION

The invention is based on the discovery of a heretofore undescribed protein, which has been named ALARM or δ-catenin, on the basis of its interaction with presenilin 1. ALARM shows a striking sequence similarity to members of the armadillo (arm)-plakoglobin-β catenin protein family. In addition, ALARM transcripts are confined almost exclusively to brain tissue.

In addition to the specific human ALARM sequences provided (or cross-referenced) herein, molecules relevant to the invention include fragments of those sequences and related polypeptides, non-peptide mimetics, and nucleic acid sequences. The invention also includes antibodies to ALARM polypeptides. These polypeptides, as well as nucleic acid encoding them, can be used for a variety of diagnostic and therapeutic applications.

In one aspect the invention features a substantially pure vertebrate ALARM polypeptide, e.g, an ALARM polypeptide from a mammal such as the human ALARM polypeptide shown in FIG. 1 (SEQ ID NO:2).

By "protein" and "polypeptide" is meant any chain of amino acids, regardless of length or post-translational modification (e.g., glycosylation or phosphorylation).

Polypeptides include, but are not limited to: recombinant polypeptides, natural polypeptides, and synthetic polypeptides as well as polypeptides which are preproteins or proproteins.

One way to ascertain purity of a preparation is by per cent dry weight. Generally, useful preparations are at least 60% by weight (dry weight) the compound of interest, i.e., an ALARM polypeptide. Preferably the preparation is at least 75%, more preferably at least 90%, and most preferably at least 99%, by weight the compound of interest. Purity can be measured by any appropriate standard method, e.g., column chromatography, polyacrylamide gel electrophoresis, or HPLC analysis. A "mature human ALARM" is the amino acid sequence shown in FIG. 1 SEQ ID NO:2.

Polypeptides substantially identical to mature human ALARM may have an amino acid sequence which is at least 85%, preferably 90%, and most preferably 95% or even 99% identical to the amino acid sequence of the ALARM polypeptide of the FIG. 1. SEQ ID NO:2. When assessing sequence identity of polypeptides, the length of the reference polypeptide sequence will generally be at least 16 amino acids, preferably at least 20 amino acids, more preferably at least 25 amino acids, and most preferably 35 amino acids. For nucleic acids, the length of the reference nucleic acid sequence will generally be at least 50 nucleotides, preferably at least 60 nucleotides, more preferably at least 75 nucleotides, and most preferably 110 nucleotides.

Sequence identity can be measured using sequence analysis software (e.g., Sequence Analysis Software Package of the Genetics Computer Group, University of Wisconsin Biotechnology Center, 1710 University Avenue, Madison, Wis. 53705).

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria.

Polypeptides corresponding to one or more domains of ALARM are also within the scope of the invention. Thus, also featured is a polypeptide including at least one antigenic determinant of ALARM, a polypeptide comprising at least one copy of the 42 amino acid arm repeat in the ALARM polypeptide, or a polypeptide comprising a βAPP binding domain of ALARM. Preferred polypeptides are those which are soluble under normal physiological conditions.

The polypeptides of the invention can be expressed fused to another polypeptide, e.g., a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

In another aspect, the invention also features a substantially pure polypeptide which includes a first portion and a second portion; the first portion includes an ALARM polypeptide and the said second portion includes a detectable marker. The first portion can be either a full-length form of ALARM or one or more domains thereof. The first portion is fused to an unrelated protein or polypeptide (i.e., a fusion partner) to create a fusion protein.

The invention also includes a pharmaceutical composition which includes an ALARM polypeptide.

In still another aspect the invention features a recombinant nucleic acid encoding an ALARM polypeptide. In one preferred embodiments the nucleic acid encodes a soluble ALARM polypeptide.

The invention also features isolated nucleic acids encoding polypeptides corresponding to one or more domains of ALARM or ALARM-related polypeptides discussed above. ALARM-encoding nucleotides can include the nucleic acids shown in FIG. 1 SEQ ID NO:1, e.g., nucleotides 366–2636 of FIG. 1 SEQ ID NO:1. Also encompassed within the invention are nucleic acid sequences that encode forms of ALARM in which sequences are altered or deleted.

By "isolated nucleic acid" is meant nucleic acid that is not immediately contiguous with both of the coding sequences with which it is immediately contiguous (one on the 5' end and one on the 3' end) in the naturally occurring genome of the organism from which it is derived. Thus, a recombinant nucleic acid could include some or all of the 5' non-coding (e.,g., promoter) sequences which are immediately contiguous to the coding sequence. The term therefore includes, for example, a recombinant DNA which is incorporated into a vector; into an autonomously replicating plasmid or virus, such as a retrovirus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

Nucleic acid sequences substantially identical to human ALARM sequences have a nucleotide sequence which is at least 85%, preferably 90%, and most preferably 95% or even 99% identical to the amino acid sequence of the ALARM polypeptide of FIG. 1 SEQ ID NO:2. For nucleic acids, the length of the reference nucleic acid sequence will generally be at least 50 nucleotides, preferably at least 60 nucleotides, more preferably at least 75 nucleotides, and most preferably 110 nucleotides.

Also within the invention are nucleic acids encoding hybrid proteins in which a portion of ALARM or a portion (e.g., one or more domains) thereof is fused to an unrelated protein or polypeptide (i.e., a fusion partner) to create a fusion protein.

The nucleic acid can be isolated either as a matter of purity or by including in it in DNA that is a non-naturally occurring molecule; for example, the DNA is not immediately contiguous with both of the sequences with which it is immediately contiguous (one on the 5' end and one on the 3' end) in the naturally occurring genome of the organism from which it is derived. Thus, a recombinant nucleic acid could include some or all of the 5' non-coding (e.,g., promoter) sequences which are immediately contiguous to the coding sequence. Other examples are a recombinant DNA which is incorporated into a vector; into an autonomously replicating plasmid or virus; or into the genomic DNA of a prokaryote or eukaryote, or which exists as a separate molecule (e.g., a CDNA or a genomic DNA fragment produced by PCR or restriction endonuclease treatment) independent of other sequences. It also includes a recombinant DNA which is part of a hybrid gene encoding additional polypeptide sequence.

The nucleic acids of the invention include nucleic acids encoding ALARM polypeptides fused to a polypeptide which facilitates secretion, e.g., a secretory sequence. Such a fused protein is typically referred to as a preprotein. The secretory sequence can be removed by the host cell to form the mature protein. Also within the invention are nucleic acids that encode mature ALARM fused to a polypeptide sequence to produce an inactive preprotein. Preproteins can be converted into the active form of the protein by removal of the inactivating sequence.

The invention also encompasses nucleic acids that hybridize under stringent conditions to a nucleic acid encoding an ALARM polypeptide. "Stringent conditions" means hybridization at 50° C. in Church buffer (7% SDS, 0.5% NaHPO$_4$, 1 mM EDTA, 1% BSA) and washing at 50° C. in 2×SSC. The hybridizing portion of the hybridizing nucleic acids are preferably 20, 30, 50, or 70 bases long. Preferably, the hybridizing portion of the hybridizing nucleic acid is 95% or even 98% identical to the sequence of a portion of a nucleic acid encoding an ALARM polypeptide. Hybridizing nucleic acids of the type described above can be used as a cloning probe, a primer (e.g., a PCR primer), or a diagnostic probe. Preferred hybridizing nucleic acids encode a polypeptide having some or all of the biological activities possessed by naturally-occurring ALARM. Hybridizing nucleic acids can be splice variants encoded by one of the ALARM genes described herein. Thus, they may encode a protein which is shorter or longer than the various forms of ALARM described herein. Hybridizing nucleic acids may also encode proteins which are related to ALARM (e.g, proteins encoded by genes which include a portion having a relatively high degree of identity to an ALARM gene described herein).

The term "nucleic acid" encompasses both RNA and DNA, including cDNA, genomic DNA, and synthetic (e.g., chemically synthesized) DNA. The nucleic acid may be double-stranded or single-stranded. Where single-stranded, the nucleic acid may be the sense strand or the antisense strand.

In yet another aspect, the invention features vectors which include a nucleic acid of the invention. In one preferred embodiment, the nucleic acid of the invention is properly positioned for expression.

By "positioned for expression" is meant that the selected DNA molecule is positioned adjacent to one or more sequence elements which direct transcription and/or translation of the sequence such that the sequence elements can control transcription and/or translation of the selected DNA (i.e., the selected DNA is operably associated with the sequence elements). Such operably associated elements can be used to facilitate the production of an ALARM polypeptide.

In a still further aspect, the invention features transformed cells harboring a nucleic acid encoding ALARM sequences discussed above.

By "transformed cell" is meant a cell into which (or into an ancestor of which) has been introduced, by means of recombinant DNA techniques, a DNA molecule encoding (as used herein) ALARM polypeptide.

The invention also features purified antibodies which specifically bind an ALARM protein or polypeptide.

By "purified antibody" is meant an antibody which is at least 60%, by dry weight, free from the proteins and naturally-occurring organic molecules with which it is naturally associated. Preferably, the preparation is at least 75%, more preferably at least 90%, and most preferably at least 99%, by dry weight, antibody.

By "specifically binds" is meant an antibody that recognizes and binds to and forms a complex with, a particular antigen, e.g., ALARM polypeptide, but which does not substantially recognize and bind to other molecules in a sample, e.g., a biological sample, which naturally includes ALARM.

The invention also features a method of diagnosing in a mammal, e.g., a human subject, an increased likelihood of, inclination toward, or susceptibility to developing a disease, in which a mutant form of the ALARM protein is a causative agent. The same method is also used to diagnose the ability of a mammal, e.g., a human, to transmit to future generations a mutant form of a protein which is a causative agent of a disease. The method involves analyzing the DNA of the mammal to determine the presence or absence of a mutation in a gene for an ALARM protein, the presence of such a mutation indicating the increased likelihood. Preferably the DNA is analyzed by amplifying the DNA with, e.g., the polymerase chain reaction, and identifying mutations in the DNA by use of the single-strand conformation polymorphism (SSCP) technique, as used and described herein, or by direct DNA sequencing.

In another aspect, the invention includes a method of inhibiting expression of an ALARM gene comprising administering to a cell containing an ALARM transcript an anti-sense ALARM oligonucleotide.

The invention also includes a method of detecting presenilin 1 in a sample, e.g., a sample taken from a human, comprising contacting the sample with an ALARM polypeptide. The sample can be from, e.g., cerebrospinal fluid.

In another aspect, the invention includes a method of diagnosing in a human subject a disease in which a mutant form of a protein which interacts with ALARM is a causative agent. The method includes analyzing a sample of fluid from the human subject to determine the presence or absence of the ALARM-interacting protein.

The invention further includes a method of diagnosing in a human subject an increased likelihood of developing or transmitting to future generations a disease in which a mutant form of a human ALARM is a causative agent. The method includes analyzing the DNA of the subject to determine the presence or absence of a mutation in a gene for an ALARM protein, the presence of such a mutation indicating the increased likelihood of transmitting the disease. The method can include, e.g., amplifying the DNA of the subject, DNA sequencing, or identifying a single strand conformation polymerism.

The invention also includes a probe or primer comprising a substantially purified single-stranded oligonucleotide, e.g., a DNA oligonucleotide, wherein the oligonucleotide contains a region which is identical to the sequence of a six-nucleotide, single-stranded segment of a gene encoding a mutant form of a human ALARM, wherein the segment comprising part or all of the mutation.

In yet another aspect, the invention includes a method of detecting an ALARM-containing complex in a biological sample by contacting the sample with an ALARM protein or an ALARM antibody and determining whether the ALARM protein or antibody binds to a component of the sample.

In a further aspect, the invention includes a method of diagnosing altered levels, e.g., lower or altered levels, of presenilin 1 in a sample by contacting the sample with ALARM and determining whether the sample contains presenilin 1 that binds to ALARM.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed descriptions, and from the claims.

BRIEF DESCRIPTION OF THE FIGURES

FIGS. 1A–1E are a schematic representation of the predicted nucleotide SEQ ID NO:1 and amino acid SEQ ID NO:2 sequence of the human ALARM protein.

FIG. 2 is a schematic representation of the ALARM arm repeats SEQ ID NOS:4–7 and their homology to the Drosophila arm sequence SEQ ID NO:3.

FIG. 3 is a.,schematic representation of the ALARM SEQ ID NO:8 and pp120SEQ ID NO:9 amino acid sequences.

FIG. 4 is a schematic representation of the ALARM SEQ ID NO:10 and γ catenin SEQ ID NO:11 amino acid sequences.

DETAILED DESCRIPTION

Previously described genes encoding proteins involved in Alzheimer's disease include βAPP, which was isolated as the cellular protein giving rise to the polypeptide fragments found in the Aβ plaques characteristic of Alzheimer's disease (reviewed in Selkoe, Ann. Rev. Cell Biol. 10:373, 1994), as well as presenilin 1 and presenilin 2, which were identified as cellular genes altered in cases of familial Alzheimer's disease (Sherrington et al., Nature 30 375:754, 1995; Levy-Lahad et al., Science 259:970, 1995; Rogaev et al., Nature 376:207, 1995).

βAPP, presenilin-1, and presenilin-2 all encode transmembrane proteins. The protein encoded by βAPP has a type I single transmembrane segment (Selkoe, supra), while the presenilin 1 and presenilin 2 polypeptides have seven putative transmembrane segments (Sherrington et al., supra, 1995; Levy-Lahad et al., Science 269:973, 1995; Rogaev et al., supra). In addition, presenilin 1 and 2 are homologous to the sel-12 gene in the nematode, *C. elegans*, which likewise encodes a protein with seven putative transmembrane segments (Leviatan et al., Nature 377:351, 1995; Grant et al., Genetics 143:237, 1996). The sel-12 gene was identified as a suppressor of defects in the lin-12 locus, which encodes a type I transmembrane protein (Sundaram et al., Genetics 135:765, 1993; Yochem et al. Nature 335:547, 1988). Based in part on this similarity, a model has been proposed in which the βAPP protein binds to the presenilin-1 or presenilin 2 gene product (Dewji et al., Science 271:159, 1996).

Until the present discovery, however, little was known about how products of the presenilin 1 and presenilin 2 genes interacted with each other, with other proteins, or whether they participated in any known signal transduction pathways. We have used the two-hybrid yeast system to identify a novel human protein on the basis of its interaction with the single hydrophilic loop region of presenilin 1. The interacting protein contains multiple copies of an amino acid repeat sequence first described in the armadillo (arm) gene in the fruit fly, *Drosophila melanogaster* (Riggleman et al., Genes Develop. 3:96, 1989). Proteins with the arm repeat have been subsequently identified in'several other proteins, including plakoglobin, β-catenin, and p120 (Peifer et al., J. Cell Biol. 118:681, 1992); Reynolds et al., Oncogene 7:2439, 1992). As other members of this family have been localized to the adherens junction, the new protein has been named ALARM, for adherens-junction linked arm protein. Alternatively, it can also be called δ-catenin, since it shows homology to known members of the catenin protein family.

Two functions have previously been ascribed to members of the arm family. First, evidence from diverse organisms suggests that arm is involved in the Wnt signal transduction pathway. Wnt homologs in a variety of organisms have been associated with signalling functions during animal development. In general, Wnt functions act so that groups of cells maintain the same identity as neighboring cells. Thus, in Drosophila the Wnt homolog, wingless (wg), acts to maintain engrailed expression in adjacent group of cells. (DiNardo et al., Nature 332:604, 1988; Martinez-Aria et al., Development 103:157, 1988).

Similarly, addition of wg, to Drosophila embryos increases the level of arm protein (Riggleman et al., Cell 63:549, 1990). This interaction is mediated through the binding of wg to cell-surface receptors encoded by members of the frizzled (Dfz) gene family (Bhanot et al., Nature 382:225, 1996). Other Drosophila genes involved in the Wng signalling pathway include dishevelled (dsh) and zeste-white 3 (zw3) (see Bhanot et al., supra).

In *Xenopus laevis* embryos, ectopic expression of β-catenin results in a phenotype similar to that caused by mutations in some member of the Wnt family (Guger et al., Dev. Biol 172:115–25). In mammalian cells, Wnt-1 expression results in the accumulation of β-catenin and plakoglobin (Hinck et al., J. Cell Biol. 124:729, 1994).

β catenin also forms a complex with the transcription factor LEF-1, and this complex localizes to the nucleus. (Behrens et al., Nature 382:638, 1996). Thus, a combination of genetic and biochemical studies suggest arm family members may be involved in transducing signals from the cell-surface to the nucleus in the Wnt pathway.

The second function in which members of the arm family have been implicated is promotion of cell adhesion. Plakoglobin, β catenin, and p120 all associate with the cytoplasmic domains of the calcium-dependent cell-cell adhesion proteins called cadherins (Daniel et al., Mol Cell. Biol. 15:4819, 1995); Shibamoto et al., J. Cell. Biol. 128:949, 1995). p120 is thought to associate with E-cadherin via E-cadherin's carboxyl terminus (Shibamoto et al., supra). Similarly, arm proteins have been localized to the cytoplasmic surface of cells and colocalize with actin. (Riggleman et al., Cell 63:549, 1990).

The present invention for the first time suggests members of the arm family are involved in the pathology of Alzheimer's disease.

ALARM Polypeptides, Proteins and Nucleic Acid Sequences

The invention encompasses, but is not limited to, ALARM proteins and polypeptides that are functionally related to ALARM encoded by the nucleotide sequence of FIG. 1 SEQ ID NO:1. Functionally related proteins and polypeptides include any protein or polypeptide sharing a functional characteristic with ALARM, e.g., the ability to bind to presenilin 1. Such functionally related ALARM polypeptides include, but are not limited to, additions or substitutions of amino acid residues within the amino acid sequence encoded by the ALARM sequences described herein which result in a silent change, thus producing a functionally equivalent gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, cryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

ALARM polypeptides and proteins of the invention can be made by altering nucleic acid sequences encoding ALARM polypeptides. While random mutations can be made to ALARM DNA (using random mutagenesis techniques well known to those skilled in the art) and the resulting mutant ALARM proteins can be tested for activity, site-directed mutations of the ALARM coding sequence can be engineered (using site-directed mutagenesis techniques well known to those skilled in the art) to generate mutant ALARMs.

To design variant ALARM polypeptides which may be altered in their function, e.g., in their ability to bind to presenilin 1, it is useful to distinguish between conserved positions and variable positions. Conserved positions are those in which the amino acid in an ALARM protein from another organism as in the same position as it is in the human ALARM protein.

To preserve ALARM function, it is preferable that conserved residues are not altered. Moreover, alteration of non-conserved residues are preferably conservative alterations, e.g., a basic amino acid is replaced by a different basic amino acid. To produce altered function variants, it is preferable to make non-conservative changes at variable and/or conserved positions. Deletions at conserved and variable positions can also be used to create altered function variants.

Other mutations to the ALARM coding sequence can be made to generate ALARMs that are better suited for expression, e.g., scaled up expression, in a selected host cell. For example, potential N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur (in N-X-S or N-X-T), and/or an amino acid deletion at the second position of any one or more of such recognition sequences, will prevent glycosylation at the modified tripeptide sequence. (See, e.g., Miyajima et al., Embo J. 5:1193, 1986).

Preferred ALARM polypeptides are those polypeptides, or variants thereof, which bind to presenilin 1 polypeptides. In determining whether a particular ALARM polypeptide or variant thereof binds to presenilin 1, one can use any assay techniques disclosed herein or in referenced publications. Preferred ALARM polypeptides and variants have 20%, 40%, 50%, 75%, 80%, or even 90% of the activity of the full-length, mature human form of ALARM described herein. Such comparisons are generally based on equal concentrations of the molecules being compared. The comparison can also be based on the amount of protein or polypeptide required to reach 50% of the maximal stimulation obtainable.

Also within the invention are fusion proteins in which a portion (e.g., one or more domains) of ALARM is fused to an unrelated protein or polypeptide (i.e., a fusion partner) to create a fusion protein. The fusion partner can be a moiety selected to facilitate purification, detection, or solubilization, or to provide some other function. Fusion proteins are generally produced by expressing a hybrid gene in which a nucleotide sequence encoding all or a portion of ALARM is joined in-frame to a nucleotide sequence encoding the fusion partner.

In general, ALARM proteins according to the invention can be produced by transformation (transfection, transduction, or infection) of a host cell with all or part of an ALARM-encoding DNA fragment (e.g., the ALARM DNA described herein) in a suitable expression vehicle. Suitable expression vehicles include: plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LACSWITCH™ Inducible Expression System (Stratagene; LaJolla, Calif.).

Those skilled in the field of molecular biology will understand that any of a wide variety of expression systems can be used to provide the recombinant protein. The precise host cell used is not critical to the invention. The ALARM protein can be produced in a prokaryotic host (e.g., E. coli or B. subtilis) or in a eukaryotic host (e.g., Saccharomyces or Pichia; mammalian cells, e.g., COS, NIH 3T3 CHO, BHK, 293, or HeLa cells; or insect cells).

Proteins and polypeptides can also be produced by plant cells. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md. ; also, see, e.g., Ausubel et al., *Current Protocols in Molecular Biology*, John Wiley & Sons, New York, 1994). The methods of transformation or transfection and the choice of expression vehicle will depend on the host system selected. Transformation and transfection methods are described, e.g., in Ausubel et al. (*Current Protocols in Molecular Biology*, John Wiley & Sons, New York, 1994); expression vehicles may be chosen from those provided, e.g., in Cloning Vectors: A Laboratory Manual (P. H. Pouwels et al., 1985, Supp. 1987).

The host cells harboring the expression vehicle can be cultured in conventional nutrient media adapted as need for activation of a chosen gene, repression of a chosen gene, selection of transformants, or amplification of a chosen gene.

One preferred expression system is the mouse 3T3 fibroblast host cell transfected with a pMAMneo expression vector (Clontech, Palo Alto, Calif.). pMAMneo provides an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding an ALARM protein would be inserted into the pMAMneo vector in an orientation designed to allow expression. The recombinant ALARM protein would be isolated as described below. Other preferable host cells that can be used in conjunction with the pMAMneo expression vehicle include COS cells and CHO cells (ATCC Accession Nos. CRL 1650 and CCL 61, respectively).

ALARM polypeptides can be produced as fusion proteins. For example, the expression vector pUR278 (Ruther et al., EMBO J. 2:1791, 1983), can be used to create lacZ fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect cell expression system, *Autographa californica* nuclear polyhidrosis virus (AcNPV), which grows in *Spodoptera frugiperda* cells, is used as a vector to express foreign genes. An ALARM coding sequence can be cloned individually into non-essential regions (for example the polyhedrin gene) of the virus and placed under control of an AcNPV promoter, e.g., the polyhedrin promoter. Successful insertion of a gene encoding an ALARM polypeptide or protein will result in inactivation of the polyhedrin gene and production of non-occluded recombinant virus (i.e., virus lacking the proteinaceous coat encoded by the polyhedrin gene). These recombinant viruses are then used to infect spodoptera frugiperda cells in which the inserted gene is expressed (see, e.g., Smith et al., J. Virol. 46:584, 1983; Smith, U.S. Pat. No. 4,215,051).

In mammalian host cells, a number of viral-based expression systems can be utilized. In cases where an adenovirus is used as an expression vector, the ALARM nucleic acid sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing an ALARM gene product in infected hosts (see, e.g., Logan, Proc. Natl. Acad. Sci. USA 81:3655, 1984.).

Specific initiation signals may also be required for efficient translation of inserted nucleic acid sequences. These signals include the ATG initiation codon and adjacent sequences. In cases where an entire native ALARM gene or ALARM cDNA, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators (Bittner et al., Methods in Enzymol. 153:516, 1987).

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, WI38, and in particular, choroid plexus cell lines.

Alternatively, an ALARM protein can be produced by a stably-transfected mammalian cell line. A number of vectors suitable for stable transfection of mammalian cells are available to the public, see, e.g., Pouwels et al. (supra); methods for constructing such cell lines are also publicly available, e.g., in Ausubel et al. (supra). In one example, cDNA encoding the ALARM protein is cloned into an expression vector that includes the dihydrofolate reductase (DHFR) gene. Integration of the plasmid and, therefore, the ALARM protein-encoding gene into the host cell chromosome is selected for by including 0.01–300 µM methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR-cells, ATCC Accession No. CRL 9096) are among the host cells preferred for DHFR selection of a stably-transfected cell line or DHFR-mediated gene amplification.

A number of other selection systems can be used, including but not limited to the herpes simplex virus thymidine kinase, hypoxanthine-guanine phosphoribosyl-transferase, and adenine phosphoribosyltransferase genes can be employed in tk, hgprt, or aprt cells, respectively. In addition, gpt, which confers resistance to mycophenolic acid (Mulligan et al., Proc. Natl. Acad. Sci. USA 78:2072, 1981); neo, which confers resistance to the aminoglycoside G-418 (Colberre-Garapin et al., J. Mol. Biol. 150:1, 1981); and hygro, which confers resistance to hygromycin (Santerre et al., Gene 30:147, 1981), can be used.

Alternatively, any fusion protein can be readily purified by utilizing an antibody specific for the fusion protein being expressed. For example, a system described in Janknecht et al., Proc. Natl. Acad. Sci. USA, 88:8972, 1991), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, ALARM or a portion thereof, can be fused to an immunoglobulin Fc domain. Such a fusion protein can be readily purified using an affinity column.

ALARM proteins and polypeptides can also be expressed in transgenic animals. Animals of any species, including, but not limited to, mice, rats, rabbits, guinea pigs, pigs, micropigs, goats, and non-human primates, e.g., baboons, monkeys, and chimpanzees, can be used to generate ALARM-expressing transgenic animals.

Any technique known in the art can be used to introduce an ALARM transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., Proc. Natl. Acad. Sci., USA 82:6148, 1985); gene targeting into embryonic stem cells (Thompson et al., Cell 56:313, 1989); and electroporation of embryos (Lo, Mol. Cell. Biol. 3:1803, 1983).

The present invention provides for transgenic animals that carry the ALARM transgene in all their cells, as well as animals that carry the transgene in some, but not all of their cells, i.e., mosaic animals. The transgene can be integrated as a single transgene or in concatamers, e.g., head-to-head tandems or head-to-tail tandems The transgene can also be selectively introduced into and activated in a particular cell type (Lasko et al., Proc. Natl. Acad. Sci. USA 89:6232, 1992). The regulatory sequences required for such a cell-type specific activation will depend upon the particular cell type of interest, and will be apparent to those of skill in the art.

When it is desired that the ALARM transgene be integrated into the chromosomal site of the endogenous ALARM gene, gene targeting is preferred. Briefly, when such a technique is to be used, vectors containing some nucleotide sequences homologous to an endogenous ALARM gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous ALARM gene in only that cell type (Gu et al., Science 265:103, 1984). The regulatory sequences required for such a cell-type specific inactivation will depend upon the particular cell type of interest, and will be apparent to those of skill in the art.

Once transgenic animals have been generated, the expression of the recombinant ALARM gene can be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of ALARM gene-expressing tissue, also can be evaluated immunocytochemically using antibodies specific for the ALARM transgene product.

Once the recombinant ALARM protein is expressed, it is isolated. Secreted forms can be isolated from the culture media, while non-secreted forms must be isolated from the host cells. Proteins can be isolated by affinity chromatography. In one example, an anti-ALARM protein antibody (e.g., produced as described herein) is attached to a column and used to isolate the ALARM protein. Lysis and fractionation of ALARM protein-harboring cells prior to affinity chromatography can be performed by standard methods (see, e.g., Ausubel et al., supra). Alternatively, an ALARM fusion protein, for example, an ALARM-maltose binding protein, an ALARM-β-galactosidase, or an ALARM-trpE fusion protein, can be constructed and used for ALARM protein isolation (see, e.g., Ausubel et al., supra; New England Biolabs, Beverly, Mass.).

Once isolated, the recombinant protein can, if desired, be further purified, e.g., by high performance liquid chromatography using standard techniques (see, e.g., Fisher, *Laboratory Techniques In Biochemistry And Molecular Biology*, eds., Work and Burdon, Elsevier, 1980).

Polypeptides of the invention, particularly short ALARM fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful ALARM fragments or analogs (described herein).

The invention also features proteins which interact with ALARM and are involved in the function of ALARM. Also included in the invention are the genes encoding these interacting proteins. Interacting proteins can be identified using methods known to those skilled in the art. One method suitable method is the "two-hybrid system," detects protein interactions in vivo (Chien et al., Proc. Natl. Acad. Sci. USA, 88:9578, 1991). A kit for practicing this method is available from Clontech (Palo Alto, Calif.).

Anti-ALARM Antibodies

Human ALARM proteins and polypeptides (or immunogenic fragments or analogs) can be used to raise antibodies useful in the invention; such polypeptides can be produced by recombinant or peptide synthetic techniques (see, e.g., *Solid Phase Peptide Synthesis*, supra; Ausubel et al., supra). In general, the peptides can be coupled to a carrier protein, such as KLH, as described in Ausubel et al., supra, mixed with an adjuvant, and injected into a host mammal. Antibodies can be purified by peptide antigen affinity chromatography.

In particular, various host animals can be immunized by injection with an ALARM protein or polypeptide. Host animals include rabbits, mice, guinea pigs, and rats. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Antibodies within the invention include monoclonal antibodies, polyclonal antibodies, humanized or chimeric antibodies, single chain antibodies, Fab fragments, F(ab')$_2$ fragments, and molecules produced using a Fab expression library.

Monoclonal antibodies, which are homogeneous populations of antibodies to a particular antigen, can be prepared using the ALARM proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In *Monoclonal Antibodies and T Cell Hybridomas*, Elsevier, N.Y., 1981; Ausubel et al., supra).

In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., Monoclonal Antibodies and Cancer Therapy, Alan R. Liss, Inc., pp. 77–96, 1983). Such antibodies can be of any immunoglobulin class including IgG, IgM, IgE, IgA, IgD and any subclass thereof. The hybridoma producing the Mab of this invention may be cultivated in vitro or in vivo. The ability to produce high titers of mAbs in vivo makes this the presently preferred method of production.

Once produced, polyclonal or monoclonal antibodies are tested for specific ALARM recognition by Western blot or immunoprecipitation analysis by standard methods, e.g., as described in Ausubel et al., supra.

Preferably, antibodies of the invention are produced using fragments of the ALARM protein which lie outside highly conserved regions and appear likely to be antigenic, by criteria such as high frequency of charged residues. In one specific example, such fragments are generated by standard techniques of PCR, and are then cloned into the PGEX expression vector (Ausubel et al., supra). Fusion proteins are expressed in *E. coli* and purified using a glutathione agarose affinity matrix as described in Ausubel, et al., supra.

Antisera can be raised by injections in a series, preferably including at least three booster injections. In some cases it may be desirable to minimize the potential problems of low affinity or specificity of antisera. In such circumstances involving fusion proteins, two or three ALARM fusion proteins can be generated for each protein, and each fusion protein can be injected into at least two rabbits.

Antisera is also checked for its ability to immunoprecipitate recombinant ALARM proteins or control proteins, such as glucocorticoid receptor, CAT, or luciferase.

The antibodies can be used, for example, in the detection of the ALARM in a biological sample as part of a diagnostic assay. Antibodies also can be used in a screening assay to measure the effect of a candidate compound on expression or localization of ALARM. Additionally, such antibodies can be used in conjunction with the gene therapy techniques described to, for example, evaluate the normal and/or engineered ALARM-expressing cells prior to their introduction into the patient. Such antibodies additionally can be used in a method for inhibiting abnormal ALARM activity.

In addition, techniques developed for the production of "chimeric antibodies" (Morrison et al., Proc. Natl. Acad. Sci., 81:6851, 1984; Neuberger et al., Nature, 312:604, 1984; Takeda et al., Nature, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine Mab and a human immunoglobulin constant region.

Alternatively, techniques described for the production of single chain antibodies (U.S. Pat. No. 4,946,778; and U.S. Pat. Nos. 4,946,778 and 4,704,692) can be adapted to produce single chain antibodies against an ALARM protein or polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science 246:1275, 1989) to allow rapid and easy identification of monoclonal Fab fragments with the desired specificity.

Antibodies to the ALARM can, in turn, be used to generate anti-idiotype antibodies that resemble a portion of ALARM using techniques well known to those skilled in the art (see, e.g., Greenspan et al., FASEB J. 7:437, 1993; Nissinoff, J. Immunol. 147:2429, 1991). For example, antibodies that bind to ALARM and competitively inhibit the binding of a ligand of ALARM can be used to generate anti-idiotypes that resemble a ligand binding domain of ALARM and, therefore, bind and neutralize a ligand of ALARM. Such neutralizing anti-idiotypic antibodies or Fab fragments of such anti-idiotypic antibodies can be used in therapeutic regimens.

ALARM Oligonucleotide Diagnostic and Therapeutic Agents

Oligonucleotide therapeutic agents can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., Proc. Natl. Acad. Sci. USA 86:6553, 1989; Lemaitre et al., Proc. Natl. Acad. Sci. USA 84:648, 1987; PCT Publication No. WO 88/09810) or the blood-brain barrier (see, e.g., PCT Publication No. WO 89/10134), or hybridization-triggered cleavage agents (see, e.g., Krol et al., BioTechniques 6:958, 1988), or intercalating agents (see, e.g., Zon, Pharm. Res. 5:539, 1988). To this end, the oligonucleotide can be conjugated to another molecule, e.g., a peptide, hybridization triggered cross-linking agent, transport agent, or hybridization-triggered cleavage agent.

The oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The oligonucleotide may also comprise at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids. Res. 15:6625, 1987). The oligonucleotide is a 2'-0-methylribonucleotide (Inoue et al., Nucl. Acids Res. 15:6131, 1987), or a chimeric RNA-DNA analog (Inoue et al., FEBS Lett. 215:327, 1987).

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (Nucl. Acids Res. 16:3209, 1988), and methylphosphonate oligonucleotides can be prepared by use of controlled pore glass polymer supports (Sarin et al., Proc. Natl. Acad. Sci. USA 85:7448, 1988).

The nucleic acid molecules should be delivered to cells that express ALARM in vivo, e.g., brain, heart, kidney, lung, uterus, endothelial cells, fibroblasts, and bone marrow stromal cells. A number of methods have been developed for delivering DNA or RNA to cells; e.g., molecules can be injected directly into the tissue site, or modified molecules, designed to target the desired cells (e.g., linked to peptides or antibodies that specifically bind receptors or antigens expressed on the target cell surface) can be administered systemically.

If intracellular concentrations of the molecule sufficient to suppress translation of endogenous mRNAs are not immediately achieved, a preferred approach uses a recombinant DNA construct in which the oligonucleotide is placed under the control of a strong pol III or pol II promoter. The use of such a construct to transfect target cells in the patient will result in the transcription of sufficient amounts of single stranded RNAs that will form complementary base pairs with the endogenous ALARM transcripts and thereby prevent translation of the ALARM MRNA. For example, a vector can be introduced in vivo such that it is taken up by a cell and directs the transcription of an RNA. Such a vector can remain episomal or become chromosomally integrated, as long as it can be transcribed to produce the desired RNA.

Such vectors can be constructed by recombinant DNA technology methods standard in the art. Vectors can be plasmid, viral, or others known in the art, used for replication and expression it mammalian cells. Expression of the-sequence encoding the RNA can be by any promoter known in the art to act in mammalian, preferably human cells. Such promoters can be inducible or constitutive. Such promoters include, but are not limited to: the SV40 early promoter region (Bernoist et al., Nature 290:304, 1981); the promoter contained in the 3' long terminal repeat of Rous sarcoma virus (Yamamoto et al., Cell 22:787-797, 1988); the herpes thymidine kinase promoter (Wagner et al., Proc. Natl. Acad. Sci. USA 78:1441, 1981); or the regulatory sequences of the metallothionein gene (Brinster et al., Nature 296:39, 1988).

Any type of plasmid, cosmid, YAC, or viral vector can be used to prepare the recombinant DNA construct which can be introduced directly into the tissue site; e.g., the brain, kidney or heart cells. Alternatively, viral vectors can be used that selectively infect the desired tissue (e.g., for brain, herpesvirus vectors may be used), in which case administration can be accomplished by another route (e.g., systemically).

Alternatively, endogenous ALARM gene expression can be reduced by targeting deoxyribonucleotide sequences complementary to the regulatory region of the ALARM gene (i.e., the ALARM promoter and/or enhancers) to form triple helical structures that prevent transcription of the ALARM

Identification of Proteins which Interact with ALARM

The invention also features proteins which interact with ALARM. For example, an ALARM protein or a fusion protein containing ALARM can be used to detect the presence of presenilin 1 in a sample. Any method suitable for detecting protein-protein interactions may be employed for identifying transmembrane proteins, intracellular, or extracellular proteins that interact with ALARM. Among the traditional methods which may be employed are co-immunoprecipitation, crosslinking and co-purification through gradients or chromatographic columns of cell lysates or proteins obtained from cell lysates and the use of ALARM to identify proteins in the lysate that interact with the ALARM. For these assays, the ALARM polypetide can be a full length ALARM, a soluble extracellular form of ALARM or some other suitable ALARM polypeptide. Once isolated, such an interacting protein can be identified and cloned and then used, in conjunction with standard techniques, to identify proteins with which it interacts. For example, at least a portion of the amino acid sequence of a protein which interacts with the ALARM can be ascertained using techniques well known to those of skill in the art, such as via the Edman degradation technique. The amino acid sequence obtained may be used as a guide for the generation of oligonucleotide mixtures that can be used to screen for gene sequences encoding the interacting protein. Screening may be accomplished, for example, by standard hybridization or PCR techniques. Techniques for the generation of oligonucleotide mixtures and the screening are well-known. (Ausubel, supra; and PCR Protocols: A Guide to Methods and Applications, 1990, Innis et al., eds. Academic Press, Inc., New York).

Additionally, methods may be employed which result directly in the identification of genes which encode proteins which interact with ALARM. These methods include, for example, screening expression libraries, in a manner similar to the well known technique of antibody probing of λgt11 libraries, using labeled ALARM polypeptide or an ALARM fusion protein, e.g., an ALARM polypeptide or domain fused to a marker such as an enzyme, fluorescent dye, a luminescent protein, or to an IgFc domain.

The method used to identify the ALARM protein, described below, based on its interaction with presenilin 1 (see also Chien et al., *Proc. Natl. Acad. Sci. USA*, 88:9578, 1991) can also be used to detect other proteins interacting with ALARM. A kit for practicing this method is available from Clontech (Palo Alto, Calif.).

Briefly, utilizing such a system, plasmids are constructed that encode two hybrid proteins: one plasmid includes a nucleotide sequence encoding the DNA-binding domain of a transcription activator protein fused to a nucleotide sequence encoding an ALARM polypeptide or protein, or an ALARM fusion protein, and the other plasmid includes a nucleolide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, ALARM may be used as the bait gene product. Total genomic or cDNA sequences are fused to the DNA encoding an activation domain. This library and a plasmid encoding a hybrid of bait ALARM gene product fused to the DNA-binding domain are cotransformed into a yeast reporter strain, and the resulting transformants are screened for those that express the reporter gene. For example, a bait ALARM gene sequence, such as ALARM or a domain of ALARM can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait ALARM gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait ALARM gene-GAL4 fusion plasmid into a yeast strain which contains a lacZ gene driven by a promoter which contains GAL4 activation sequence. A cDNA encoded protein, fused to GAL4 transcriptional activation domain, that interacts with bait ALARM gene product will reconstitute an active GAL4 protein and thereby drive expression of the HIS3 gene. Colonies which express HIS3 can then be purified from these strains, and used to produce and isolate the bait ALARM gene-interacting protein using techniques routinely practiced in the art.

In addition, a genetic test can also be used wherein ALARM nucleic acid sequences are used to identify polymorphisms in the ALARM gene which indicate an increased likelihood of developing a condition or disease.

Diagnosis of Diseases Associated with Alterations in ALARM Nucleic Acid Sequences The invention disclosed herein also relates to diagnosis of various diseases by first identifying the genetic defect in ALARM which causes the disease in question, and then devising an assay using either a hybridization probe or a PCR amplification primer containing the mutant sequence.

After identifying a specific ALARM mutation that is associated with a particular disease, that information can then be used to design an oligonucleotide useful as a diagnostic tool to screen other individuals for that particular disease.

The oligonucleotide can take the form of a hybridization probe or a primer for PCR amplification. Such hybridization probes could range in size from six to 10,000 nucleotides (preferably 13 to 20 nucleotides), while PCR primers could range from ten to 1000 nucleotides (preferably 18 to 25 nucleotides).

If either such screen reveals that the mutation appears in some patients with an autosomal dominant disease but in no unaffected individuals of a statistically significant sample, it can be presumed that the existence of that mutation in the DNA of any tested individual will be informative for the inherited propensity to develop one form of autosomal dominant ALARM-protein related disease. An oligonucleotide which includes the mutant sequence will be useful as a diagnostic tool for screening individuals for that form of the disease. A genetic screening test based on this oligonucleotide, and further including a second oligonucleotide with the normal sequence could be useful not only to detect those homozygous for the mutation (and thus destined to develop the disease), but also those heterozygous for the mutation (and thus carriers of the disease trait).

A genetic screening test can also be used to identify individuals with autosomal recessive ALARM-associated disease, and/or to identify compound heterozygotes. In the latter case, two different mutations, each affecting different copies of the disease gene, are present in the affected patients of a sibship. Each of the two mutations comes from one parent.

Uses of the Invention

The ALARM proteins and nucleic acids of the invention have a variety of uses. For example, an ALARM polypeptide can be used to determine the amount of ALARM-binding presenilin 1 in a sample.

In addition, ALARM antibodies can be used in an immunoassay to monitor the level of ALARM produced by a mammal and also to determine the subcellular location of ALARM in a mammal.

Further, both ALARM polypeptides and ALARM antibodies can be used to identify additional proteins which bind to ALARM.

ALARM nucleic acids can also be used to identify human chromosome 5, as diagnostic agents to identify individuals with mutations in ALARM nucleic acid sequences. In addition, ALARM nucleic acid and polypeptide sequences be used as molecular weight markers and also to block expression of ALARM sequences.

EXAMPLES

The invention will be further described in the following examples, which do not limit the scope of the invention described in the claims. The following examples illustrate the characterization of human ALARM nucleic acids and polypeptides.

Example 1

Primary Structure of ALARM Nucleic Acids and Polypeptides

The yeast two-hybrid system was used to identify cDNAs from a human brain cDNA library that bind to the Loop region of presenilin 1.

PCR was used to amplify the presenilin 1 loop region, which is defined by EcoRI and BamHI sites at it 5' or 3' ends, respectively and which encodes amino acids 260–400 of presenilin. The PCR products and vector PAS2-1 DNA were digested with these two restriction enzymes and then ligated. The resulting construct was confirmed by sequence analysis and named the Loop construct.

Standard procedures were used to identify brain. cDNAS that encoded proteins binding to the Loop region. Briefly, the plasmid DNA for the controls of the yeast two hybrid experiment was from the MATCHMAKER II kit (Clontech) which includes pCL1 (full length Gal 4), pVA3-1 (P53 to Gal 4 binding domain), pTD1-1 (SV40 large T-antigen to activation domain), pLAM 5'-1 (Human lamin C to BD).

Plasmid DNAs were introduced into yeast strain 190, Strain 190 was transformed first with the Loop plasmid and with a human brain cDNA library (the Matchmaker library). In each case, selection for transformants was made on appropriate selective medium.

Plasmid DNA from presumptive colonies containing an interacting cDNA was isolated from a single, well-isolated colony using standard procedures. The plasmid DNA was then transformed into E. coli, from which plasmid DNA was prepared.

Using the Loop region as bait, eight colonies were identified in the two hybrid assay. Two colonies were positive upon rescreening, and they were found to carry the identical insert.

To verify that the interaction between the "captured protein" and the Loop region was not an artifact of the two hybrid system, the insert was transcribed and translated in vitro, and the resulting protein was tested for its ability to bind a Loop-glutathione S-transferase protein.

Fresh overnight cultures of E. coli transformed with pGex-4T-1 or one of its recombinants were diluted 1:10 in LB-Amp and incubated for 2 hours at 37C. with shaking until the $A_{6C0}$ reached 0.6–1.0. IPTG was added to a final concentration of 0.1 mM and the culture was incubated for an additional 3hours. The cells were washed once with PBS, and resuspended in 1 ml PBS plus protease inhibitors (PMSF, aprotinin, leupeptin, pepstatin) in microfuge tubes and then lysed by mild sonication. Triton X-100 in PBS was then added to a final concentration of 1%. The lysate was rotated at 4° C. for 20 minutes followed by centrifugation at 14,000 for 10 minutes at 4° C.

The supernatant was rocked for 15–30 minutes at 4° C. with 20 $\mu$l of 50% (v/v) glutathione-sepharose, which had been previously washed with PBS. After centrifugation, the beads were washed three times with PBS.

In vitro translation was performed using Promega (Madison, Wis.) TNT kits. Briefly, 1–2 ug of plasmid DNA was mixed with 25 ul of TnT rabbit reticulocyte lysate, 2 ul reaction buffer, 1 ul T7 RNA polymerase, 2 ul amino acid mixture minus methionine, 4 ul $^{35}$S-methionine, 1 ul Rnasin and $H_2O$ in a 50 ul reaction volume. The reaction was incubated at 30° C. for 2 hours.

In vitro translated proteins were mixed in binding buffer (10 mM Tris-HCl, pH 8.0; 200 mM NaCl; 5 mM EDTA, 0.5% NP-40, 1 mM DTT, 3 mg/ml of BSA, and proteinase inhibitors) with 20 ul of protein A agarose and rocked at 4° C. for 1 hour. Antibody was added to the precleared supernatant (1:200), and rocked for 2 hours at 40° C. and then 20 ul of protein-A agarose was added and rocked for another 2 hours. The beads were washed then washed 4 times.

Glutathione-sepharose beads bound with GST-fusion proteins were washed with binding buffer (10 mM Tris-HCl, pH 8.0; 200 mM NaCl; 5 mM EDTA, 0.5% NP-40, 1 mM DTT, 3 mg/ml of BSA, and proteinase inhibitors), rocked with aliquots of in vitro translated $^{35}$S-labeled proteins for 1 hour at 4° C. in binding buffer. The beads were washed five times with binding buffer and boiled in sample buffer. The eluted proteins were then analyzed on SDS-PAGE. Binding of the captured protein to the Loop-glutathione S-transferase protein was observed, confirming that the captured protein was not an artifact of the yeast two-hybrid system.

The DNA encoding the captured protein was then sequenced. Sequence analysis was performed using the GCG sequence analysis program.

The captured protein was found to have the DNA sequence shown in FIG. 1 SEQ ID NO:1, and encode a protein with the amino acid sequence shown in FIG. 1 SEQ ID NO:2. The protein contains four copies of a the arm repeat, which was originally identified in the *Drosophila melanogaster* arm gene and has been subsequently identified in members of the catenin family. Because members of the catenin family have been associated with the adherens junctions, the new protein has been named ALARM, for adherens-junction linked arm protein, or, alternatively, δ catenin. The presence of the arm repeats in the ALARM protein, and their similarity to the original arm repeat is shown in FIG. 2. The arm repeats from the ALARM sequence are represented labeled as 1 SEQ ID NO:4, SEQ ID NO:5, SEQ ID NO:6, and SEQ ID NO:7. Repeat ii SEQ ID NO:5 is most homologous to arm, SEQ ID NO:3 with 70% homology, while repeat iii SEQ ID NO:6 is the least homologous, with 31% homology.

Among proteins identified which contain arm repeats, ALARM shows the highest homology to ppl20, a protein originally identified as a substrate for the tyrosine kinase pp6osrc (Staddon et al., J. Cell Biol. 130:369, 1995). The. ppl120 homology is shown in FIG. 3. Overall, ALARM SEQ ID NO:8 is 60.8% similar and 43.3% identical to ppl120 SEQ ID NO:9.

The sequence alignment between ALARM and γ catenin, is shown in FIG. 4. Overall, ALARM SEQ ID NO:10 and γ catenin SEQ ID NO:11 are 52.3% similar and 32.1% identical.

In chromosomal mapping studies, DNA sequences homologous to ALARM-encoding DNA sequences were found to map to chromosome 5.

Example 2

Tissue Localization of ALARM RNA Sequences

To determine the tissues in which ALARM sequences are transcribed, poly A$^+$ RNA was isolated from several human tissues.

RNA was isolated from human tissues using standard procedures. RNA hybridization was performed using Clontech ExpressHyb solution. Briefly, the ExpressHyb Solution was warmed up to 60° C. The nylon membrane was prehybridized in 5 ml of ExpressHyb Solution with continuous shaking at 60° C. for 30 minutes. Denatured ALARM DNA (labeled with $^{32}$P by random primer extension) was added to 5 ml of fresh ExpressHyb to a final activity 10$^6$ cpm/ml, and the hybridization was carried out for 1 hour at 60° C. The blot was rinsed in wash solution 1 several times at room temperature for 30–40 minutes with continuous agitation, and then washed in wash solution 2 with continuous shaking at 500C for 40 minutes with one change of fresh solution. The blot was then exposed to x-ray film at –70° C. with two intensifying screens.

An intensely hybridizing band 6 kb in size was detected in tissue from brain, as were minor bands of 7 kb and 4.0kb. A weak to moderately hybridizing band of 6 kb was detected in the pancreas. Heart tissue gave rise to barely detectable transcripts, and no hybridization was detected in skeletal muscle, kidney, liver, placenta, or lung. These data indicate that ALARM expression is found nearly exclusively in brain tissue.

Example 3

Generation of Antibodies Against ALARM Peptides and Co-immunoprecipitation Experiments Using ALARM Anti-Sera Polyclonal anti-ALARM antibodies were raised using standard procedures by injecting a synthetic 14 amino acid peptide having the sequence YETSHYPASPDSWVSEQ ID NO:13, corresponding to the 14 carboxy terminal residues of the ALARM protein,into rabbits. Anti-alarm antibodies were also raised against a GST-fusion protein containing the 100 amino terminal amino acids of ALARM as shown in FIG. 1 SEQ ID NO:2. Antibodies raised to the peptides detected a protein migrating with a size of about 130 kDa.

To determine if ALARM binds cadherin or the β-amyloid precursor protein (βAPP) protein, co-immunoprecipitation experiments were performed in which anti-ALARM sera was used in co-immunoprecipitation experiments using ALARM and each of the respective proteins. Anti-ALARM sera precipitated cadherin protein when ALARM and cadherin proteins were coexpressed in vitro. Anti-Alarm antisera also immunoprecipitated cadherin in isolated brain tissues. This suggests that ALARM and cadherin interact directly. In addition, because cadherin is found at the adherens junction, it indicates ALARM also localizes to this structure.

Anti ALARM sera also co-precipitated the βAPP precursor peptide when these proteins were coexpressed in vitro. This result suggests that ALARM and the APPβ protein bind directly, and that ALARM may be involved in generating the Aβ peptide.

Example 4

Cellular Localization of ALARM Polypeptides

Immunolocalization studies examining ALARM expression in neurons cultured from embryonic day 18 rat brains were performed using an anti-ALARM antibody isolated as described in Example 3. Rat brains showed neuronal staining primarily in the cell body. The observed pattern is consistent with the reported expression pattern of presenilin 1.

Example 5

Diagnostic Assays Utilizing ALARM Hybridization Probes

As described above, a nucleic acid probe containing some or all of the ALARM-encoding sequences of the invention is used to detect ALARM mRNA in a sample of cells (e.g., brain cells) suspected of having altered ALARM expression. The probe used is a single-stranded DNA or RNA (preferably DNA) antisense to the ALARM coding sequence. It is produced by synthetic or recombinant DNA methods, and labelled with a radioactive tracer or other standard detecting means. The probe includes from 15 up to the full ALARM coding sequence, and preferably is at least 30 nucleotides long. The assay is carried out by standard methods of in situ hybridization or Northern analysis, using stringent hybridization conditions. Control hybridization assays are run in parallel using normal cells or tissue sections from the same type of tissue as the test sample, and/or cells from a known tissue or cell line, or a tissue section, whose ALARM transcription levels are known. Cells which exhibit an altered level of hybridization to the probe, compared to the level seen with normal epithelial cells, are likely to be indicative of a neurological condition. The amount of hybridization is quantitated by standard methods, such as counting the grains of radioactivity-exposed emulsion on an in situ hybridization assay of a biopsy slide, or by densitometric scan of a Northern blot X-ray film. Alternatively, comparison of the test assay results with the results of the control assays is relative rather than quantitative, particularly where the difference in levels of hybridization is dramatic.

Example 6

Diagnostic Assays Utilizing Alarm Antibodies

Antibodies specific for ALARM are generated by standard polyclonal or monoclonal methods, using as immunogen a purified, naturally-occurring ALARM; recombinant ALARM; or any antigenic fragment of ALARM (e.g., the peptides described above) which induces antibodies that react with naturally-occurring ALARM. The latter fragment can be produced by synthetic or recombinant methods, or by proteolytic digestion of ALARM. If desired, the antigenic fragment is linked by standard methods to a molecule which increases the immunogenicity of the fragment, such as keyhole limpet hemocyanin (as described above). The polyclonal or monoclonal antibodies so produced are screened using purified recombinant or naturally occurring ALARM, or as described above, to select those which form an immunocomplex with ALARM specifically.

The antibodies so produced are employed in diagnostic methods for detecting cells, tissues, or biological fluids in which the presence of ALARM is altered relative to normal cells, an indication that the patient has a neurological condition. The sample tested may be a fixed section of a tissue biopsy, a preparation of cells obtained from a suspect tissue, or a sample of biological fluid, such as cerebrospinal fluid. Standard methods of immunoassay may be used, including those described above as well as sandwich ELISA. If the tested cells express altered levels of ALARM protein in this assay relative to normal cells of the same tissue type, the tested cells are likely to represent a neurological condition. The anti-ALARM antibodies are also used to detect alterations in the levels or ALARM-binding activity of other cellular components, e.g., presenilin-1, cadherein, or βAPP protein, that interact with ALARM. Anti-ALARM antibodies are used to detect these proteins using co-immunoprecipitation assays known in the art.

Example 7

Screens for and Uses of Therapeutic Agents Based on their Interaction with ALARM Cells in which the expression or activity of the endogenous ALARM gene is altered, i.e., down-regulated, are used as a screening tool to identify compounds or treatment strategies that increase expression or activity of the ALARM gene.

The cells are treated in vitro with the candidate compounds, and the amount of ALARM expression is determined using either a hybridization assay (e.g., Northern analysis) or an immunoassay. If a given compound is found to increase ALARM expression, it is then further tested to see whether treatment with the compound prevents the development of a neurological condition in vivo in an appropriate animal model. An appropriate animal model is a transgenic model constructed using the techniques described above in which a ALARM gene is expressed under the control of an inducible promoter.

A compound effective both in increasing ALARM expression or activity (e.g., in facilitating its binding to presenilin 1 or βAPP) is a potential therapeutic useful for the treatment of conditions in which ALARM expression is increased compared to normal cells. Further evaluation of the clinical usefulness of such a compound follows standard methods of evaluating toxicity and clinical effectiveness of agents for treating neurological conditions.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An isolated nucleic acid molecule, wherein said molecule comprises a nucleotide sequence encoding a polypeptide having a sequence that is at least 85% identical to the sequence of the human ALARM polypeptide shown in FIG. 1 (SEQ ID NO:2).

2. The nucleic acid molecule of claim 1, wherein said nucleotide sequence encodes a polypeptide that binds presenilin-1.

3. The nucleic acid molecule of claim wherein said molecule encode s the polypeptide shown in FIG. 1 (SEQ ID NO:2).

4. The isolated nucleic acid molecule of claim 1, said molecule comprising the nucleotide sequence shown in FIG. 1 (SEQ ID NO:1).

5. An isolated nucleic acid molecule encoding an ALARM polyieptide, said molecule hybridizing to the complement of the nucleic acid sequence shown in FIG. 1 (SEQ ID NO:1 ) at 50° C. in Church Buffer (7% SDS, 0.5% NaHPO$_4$, 1 mM EDTA, 1%BSA) and washing at 50C. in 2×SSC.

6. A vector comprising the recombinant nucleic acid of claim 1.

7. A cell comprising the recombinant nucleic acid of claim 1.

8. The nucleic acid molecule of claim 5, wherein said molecule encodes the polypeptide shown in FIG. 1 (SEQ ID NO:2).

9. The isolated nucleic acid molecule of claim 5, said molecule comprising the nucleotide sequence shown in FIG. 1 (SEQ ID NO:1).

10. A vector comprising the recombinant nucleic acid of claim 5.

11. A cell comprising the recombinant nucleic acid of claim 5.

* * * * *

UNITED STATES PATENT AND TRADEMARK OFFICE
CERTIFICATE OF CORRECTION

PATENT NO. : 6,797,511 B1
APPLICATION NO. : 09/629498
DATED : September 28, 2004
INVENTOR(S) : Kenneth S. Kosik and Jianhua Zhou It is certified that error appears in the above-identified patent and that said Letters Patent is hereby corrected as shown below:

Title Page, Item (56) References Cited, OTHER PUBLICATIONS, first column, in the Daniel et al. reference, "β-Catenin" should be -- α-Catenin --.

Title Page, Item (56) References Cited, OTHER PUBLICATIONS, second column, in the Rubinfeld et al. reference, "62-Catenin" should be -- β-Catenin --.

Column 51, line 41, after "claim", insert -- 1 --.

Column 51, line 42, "encode s" should be -- encodes --.

Column 51, line 47, "polyieptide" with -- polypeptide --.

Signed and Sealed this

Eighteenth Day of December, 2007

JON W. DUDAS
*Director of the United States Patent and Trademark Office*

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 2983 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 366...2633

(xi) SEQUENCE DESCRIPTION: SEQ ID NO: 1:

```
GCACCAGCTC GCCCATCAAC ATCGTCGTGT CCTCGGCCGG CCTGTCCCCG ATCCGCGTGA     60

CCTCGCCCCC CACCGTGCAG TCCACCATCT CCTCCTCGCC CATCCACCAG CTGAGCTCCA    120
```

```
CCATCGGCAC GTACGCCACC CTGTCGCCCA CCAAGCGCCT GGTCCACGCG TCCGAGCAGT    180

ACAGCAAGCA CTCGCAGGAG CTGTATGCCA CGGCCACCCT CCAGAGGCCG GGCAGCCTGG    240

CAGCTGGTTC CCGAGCCTCA TACAGCAGCC AGCATGGGCA CCTGGGCCCA GAGTTGCGGG    300

CCCTGCAGTC CCCAGAACAC CACATAGATC CCATCTATGA AGTCCGCGTC TATCAGAAGC    360

CCCCT ATG AGG AGT CTC AGC CAG AGC CAG GGG GTC CCT CTG CCG CCA GCA   410
      Met Arg Ser Leu Ser Gln Ser Gln Gly Val Pro Leu Pro Pro Ala
       1               5                  10                  15

CAC ACC GGC ACC TAC CGC ACG AGC ACA GCC CCA TCT TCC CCT GGT GTC     458
His Thr Gly Thr Tyr Arg Thr Ser Thr Ala Pro Ser Ser Pro Gly Val
                 20                  25                  30

GAC TCC GTC CCC TTG CAG CGC ACA GGC AGC CAG CAC GGC CCA CAG AAT     506
Asp Ser Val Pro Leu Gln Arg Thr Gly Ser Gln His Gly Pro Gln Asn
             35                  40                  45

GCC GCC GCG GCC ACC TTC CAG AGG GCC AGC TAT GCC GCC GGC CCA GCC     554
Ala Ala Ala Ala Thr Phe Gln Arg Ala Ser Tyr Ala Ala Gly Pro Ala
         50                  55                  60

TCC AAT TAC GCG GAC CCC TAC CGA CAG CTG CAG TAT TGT CCC TCT GTT     602
Ser Asn Tyr Ala Asp Pro Tyr Arg Gln Leu Gln Tyr Cys Pro Ser Val
     65                  70                  75

GAG TCT CCA TAC AGC AAA TCC GGC CCT GCT CTC CCG CCT GAA GGC ACC     650
Glu Ser Pro Tyr Ser Lys Ser Gly Pro Ala Leu Pro Pro Glu Gly Thr
 80                  85                  90                  95

TTG GCC AGG TCC CCG TCC ATT GAT AGC ATT CAG AAA GAT CCC AGA GAA     698
Leu Ala Arg Ser Pro Ser Ile Asp Ser Ile Gln Lys Asp Pro Arg Glu
                100                 105                 110

TTT GGA TGG AGA GAC CCG GAA CTG CCG GAA GTG ATT CAG ATG TTG CAG     746
Phe Gly Trp Arg Asp Pro Glu Leu Pro Glu Val Ile Gln Met Leu Gln
            115                 120                 125

CAC CAG TTT CCC TCG GTC CAG TCT AAC GCG GCA GCC TAC TTG CAA CAC     794
His Gln Phe Pro Ser Val Gln Ser Asn Ala Ala Ala Tyr Leu Gln His
        130                 135                 140

CTC TGT TTT GGA GAC AAC AAA ATT AAA GCC GAG ATA AGG AGA CAA GGA     842
Leu Cys Phe Gly Asp Asn Lys Ile Lys Ala Glu Ile Arg Arg Gln Gly
    145                 150                 155

GGC ATC CAG CTC CTG GTG GAC CTG TTG GAT CAT CGG ATG ACC GAA GTC     890
Gly Ile Gln Leu Leu Val Asp Leu Leu Asp His Arg Met Thr Glu Val
160                 165                 170                 175

CAC CGT AGT GCC TGT GGA GCT CTG AGA AAC CTG GTG TAT GGG AAG GCC     938
His Arg Ser Ala Cys Gly Ala Leu Arg Asn Leu Val Tyr Gly Lys Ala
                180                 185                 190

AAC GAT GAT AAC AAA ATT GCC CTG AAA AAC TGT GGT GGC ATC CCA GCA     986
Asn Asp Asp Asn Lys Ile Ala Leu Lys Asn Cys Gly Gly Ile Pro Ala
            195                 200                 205

CTG GTG AGG TTA CTC CGC AAG ACG ACT GAC CTG GAG ATC CGG GAG CTG    1034
Leu Val Arg Leu Leu Arg Lys Thr Thr Asp Leu Glu Ile Arg Glu Leu
        210                 215                 220

GTC ACA GGA GTC CTT TGG AAC CTC TCC TCA TGC GAT GCA CTC AAA ATG    1082
Val Thr Gly Val Leu Trp Asn Leu Ser Ser Cys Asp Ala Leu Lys Met
    225                 230                 235

CCA ATC ATC CAG GAT GCC CTA GCA GTA CTG ACC AAC GCG GTG ATT ATC    1130
Pro Ile Ile Gln Asp Ala Leu Ala Val Leu Thr Asn Ala Val Ile Ile
240                 245                 250                 255

CCC CAC TCA GGC TGG GAA AAT TCG CCT CTT CAG GAT GAT CGG AAA ATA    1178
Pro His Ser Gly Trp Glu Asn Ser Pro Leu Gln Asp Asp Arg Lys Ile
                260                 265                 270

CAG CTG CAT TCA TCA CAG GTG CTG CGT AAC GCC ACC GGG TGC TTA AGG    1226
Gln Leu His Ser Ser Gln Val Leu Arg Asn Ala Thr Gly Cys Leu Arg
            275                 280                 285
```

-continued

| | |
|---|---|
| AAT GTT AGT TCG CCC GGA GAG GAG GCC CGC AGA AGG ATG AGA GAG TGT<br>Asn Val Ser Ser Pro Gly Glu Glu Ala Arg Arg Arg Met Arg Glu Cys<br>          290                    295                    300 | 1274 |
| GAT GGG CTT ACG GAT GCC TTG CTG TAC GTG ATC CAG TCT GCG CTG GGG<br>Asp Gly Leu Thr Asp Ala Leu Leu Tyr Val Ile Gln Ser Ala Leu Gly<br>305                    310                    315 | 1322 |
| AGC AGT GAG ATC GAT AGC AAG ACC GTT GAA AAC TGT GTG TGC ATT TTA<br>Ser Ser Glu Ile Asp Ser Lys Thr Val Glu Asn Cys Val Cys Ile Leu<br>320                    325                    330                    335 | 1370 |
| AGG AAC CTC TCG TAC CGG CTG GCG GCA GAA ACG TCT CAG GGA CAG CAC<br>Arg Asn Leu Ser Tyr Arg Leu Ala Ala Glu Thr Ser Gln Gly Gln His<br>          340                    345                    350 | 1418 |
| ATG GGC ACG GAC GAG CTG GAC GGG CTA CTC TGT GGC GAG GCC AAT GGC<br>Met Gly Thr Asp Glu Leu Asp Gly Leu Leu Cys Gly Glu Ala Asn Gly<br>               355                    360                    365 | 1466 |
| AAG GAT GCT GAG AGC TCT GGG TGC TGG GGC AAG AAG AAG AAG AAA AAG<br>Lys Asp Ala Glu Ser Ser Gly Cys Trp Gly Lys Lys Lys Lys Lys Lys<br>          370                    375                    380 | 1514 |
| AAA TCC CAA GAT CAG TGG GAT GGA GTA GGA CCT CTT CCA GAC TGT GCT<br>Lys Ser Gln Asp Gln Trp Asp Gly Val Gly Pro Leu Pro Asp Cys Ala<br>385                    390                    395 | 1562 |
| GAA CCA CCA AAA GGG ATC CAG ATG CTG TGG CAC CCA TCA ATA GTC AAA<br>Glu Pro Pro Lys Gly Ile Gln Met Leu Trp His Pro Ser Ile Val Lys<br>400                    405                    410                    415 | 1610 |
| CCC TAC CTC ACA CTG CTC TCT GAG TGC TCA AAT CCA GAC ACG CTG GAA<br>Pro Tyr Leu Thr Leu Leu Ser Glu Cys Ser Asn Pro Asp Thr Leu Glu<br>               420                    425                    430 | 1658 |
| GGG GCG GCA GGC GCC CTG CAG AAC TTG GCT GCA GGG AGC TGG AAG TGG<br>Gly Ala Ala Gly Ala Leu Gln Asn Leu Ala Ala Gly Ser Trp Lys Trp<br>          435                    440                    445 | 1706 |
| TCA GTA TAT ATC CGA GCC GCT GTC CGA AAA GAG AAA GGC CGG CCC ATC<br>Ser Val Tyr Ile Arg Ala Ala Val Arg Lys Glu Lys Gly Arg Pro Ile<br>          450                    455                    460 | 1754 |
| CTC GTG GAG CTG CTC CGA ATA GAC AAT GAC CGT GTG GCG TGC GCG GTG<br>Leu Val Glu Leu Leu Arg Ile Asp Asn Asp Arg Val Ala Cys Ala Val<br>465                    470                    475 | 1802 |
| GCC ACT GCG CTG CGG AAC ATG GCC TTG GAC GTC AGA AAT AAG GAG CTC<br>Ala Thr Ala Leu Arg Asn Met Ala Leu Asp Val Arg Asn Lys Glu Leu<br>480                    485                    490                    495 | 1850 |
| ATC GGC AAA TAC GCC ATG CGA GAC CTA GTC CAC AGG CTT CCA GGA GGG<br>Ile Gly Lys Tyr Ala Met Arg Asp Leu Val His Arg Leu Pro Gly Gly<br>               500                    505                    510 | 1898 |
| AAC AAC AGC AAC AAC ACT GCA AGC AAG GCC ATG TCG GAT GAC ACA GTG<br>Asn Asn Ser Asn Asn Thr Ala Ser Lys Ala Met Ser Asp Asp Thr Val<br>          515                    520                    525 | 1946 |
| ACA GCT GTC TGC TGC ACA CTG CAC GAA GTG ATT ACC AAG AAC ATG GAG<br>Thr Ala Val Cys Cys Thr Leu His Glu Val Ile Thr Lys Asn Met Glu<br>               530                    535                    540 | 1994 |
| AAC GCC AAG GCC TTA CGG GAT GCC GGT GGC ATC GAG AAG TTG GTC GGC<br>Asn Ala Lys Ala Leu Arg Asp Ala Gly Gly Ile Glu Lys Leu Val Gly<br>          545                    550                    555 | 2042 |
| ATC TCC AAA AGC AAA GGA GAT AAA CAC TCT CCA AAA GTG GTC AAG GCT<br>Ile Ser Lys Ser Lys Gly Asp Lys His Ser Pro Lys Val Val Lys Ala<br>560                    565                    570                    575 | 2090 |
| GCA TCT CAG GTC CTC AAC AGC ATG TGG CAG TAC CGA GAT CTG AGG AGT<br>Ala Ser Gln Val Leu Asn Ser Met Trp Gln Tyr Arg Asp Leu Arg Ser<br>               580                    585                    590 | 2138 |
| CTC TAC AAA AAG GAT GGA TGG TCA CAA TAC CAC TTT GTA GCC TCG TCT<br>Leu Tyr Lys Lys Asp Gly Trp Ser Gln Tyr His Phe Val Ala Ser Ser | 2186 |

-continued

```
              595                 600                 605
TCA ACC ATC GAG AGG GAC CGG CAA AGG CCC TAC TCC TCC TCC CGC ACG    2234
Ser Thr Ile Glu Arg Asp Arg Gln Arg Pro Tyr Ser Ser Ser Arg Thr
        610                 615                 620

CCC TCC ATC TCC CCT GTG CGC GTG TCT CCC AAC AAC CGC TCA GCA AGT    2282
Pro Ser Ile Ser Pro Val Arg Val Ser Pro Asn Asn Arg Ser Ala Ser
        625                 630                 635

GCC CCA GCT TCA CCT CGG GAA ATG ATC AGC CTC AAA GAA AGG AAA ACA    2330
Ala Pro Ala Ser Pro Arg Glu Met Ile Ser Leu Lys Glu Arg Lys Thr
640                 645                 650                 655

GAC TAC GAG TGC ACC GGC AGC AAC GCC ACC TAC CAC GGA GCT AAA GGC    2378
Asp Tyr Glu Cys Thr Gly Ser Asn Ala Thr Tyr His Gly Ala Lys Gly
                660                 665                 670

GAA CAC ACT TCC AGG AAA GAT GCC ATG ACA GCT CAA AAC ACT GGA ATT    2426
Glu His Thr Ser Arg Lys Asp Ala Met Thr Ala Gln Asn Thr Gly Ile
            675                 680                 685

TCA ACT TTG TAT AGG AAT TCT ACA AGA AAT TAC GAT GAG TCC TTC TTC    2474
Ser Thr Leu Tyr Arg Asn Ser Thr Arg Asn Tyr Asp Glu Ser Phe Phe
            690                 695                 700

GAG GAC CAG GTC CAC CAT CGC CCT CCC GCC AGC GAG TAC ACC ATG CAC    2522
Glu Asp Gln Val His His Arg Pro Pro Ala Ser Glu Tyr Thr Met His
        705                 710                 715

CTG GGT CTC AAG TCC ACC GGC AAC TAC GTT GAC TTC TAC TCA GCT GCC    2570
Leu Gly Leu Lys Ser Thr Gly Asn Tyr Val Asp Phe Tyr Ser Ala Ala
720                 725                 730                 735

CGT CCC TAC AGT GAA CTG AAC TAT GAA ACG AGC CAC TAC CCG GCC TCC    2618
Arg Pro Tyr Ser Glu Leu Asn Tyr Glu Thr Ser His Tyr Pro Ala Ser
                740                 745                 750

CCC GAC TCC TGG GTG TGAGGAGCAG GGCACAGGCG CTCCGGGAAC AGTGCATGTG    2673
Pro Asp Ser Trp Val
                755

CATGCATACC ACAAGACATT TCTTTCTGTT TTGTTTTTTT CTCCTGCAAA TTTAGTTTGT    2733

TAAAGCCTGT TCCATAGGAA GGCTGTGATA ACCAGTAAGG AAATATTAAG AGCTATTTTA    2793

GAAAGCTAAA TGAATCGCAA GTTTAACTTG GAAATCAGTA GAAAGCTAAA GTGATCCTAA    2853

ATATGACAGT GGGCAGCACC TTTCTAGCGT GAGCTGTAAA GTAACGANAA GTGCTTTATA    2913

CTGAACGTNG TTGATGGGAG GANANACAAG CATTCCGGCC GGTGGGGCNT ANGGTTNTCN    2973

TTAACACAAT                                                          2983
```

(2) INFORMATION FOR SEQ ID NO: 2:

(i) SEQUENCE CHARACTERISTICS:
        (A) LENGTH: 756 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 2:

```
Met Arg Ser Leu Ser Gln Ser Gln Gly Val Pro Leu Pro Pro Ala His
  1               5                  10                  15

Thr Gly Thr Tyr Arg Thr Ser Thr Ala Pro Ser Ser Pro Gly Val Asp
                 20                  25                  30

Ser Val Pro Leu Gln Arg Thr Gly Ser Gln His Gly Pro Gln Asn Ala
             35                  40                  45

Ala Ala Ala Thr Phe Gln Arg Ala Ser Tyr Ala Ala Gly Pro Ala Ser
         50                  55                  60
```

-continued

```
Asn Tyr Ala Asp Pro Tyr Arg Gln Leu Gln Tyr Cys Pro Ser Val Glu
 65                  70                  75                  80

Ser Pro Tyr Ser Lys Ser Gly Pro Ala Leu Pro Pro Glu Gly Thr Leu
             85                  90                  95

Ala Arg Ser Pro Ser Ile Asp Ser Ile Gln Lys Asp Pro Arg Glu Phe
            100                 105                 110

Gly Trp Arg Asp Pro Glu Leu Pro Glu Val Ile Gln Met Leu Gln His
        115                 120                 125

Gln Phe Pro Ser Val Gln Ser Asn Ala Ala Tyr Leu Gln His Leu
    130                 135                 140

Cys Phe Gly Asp Asn Lys Ile Lys Ala Glu Ile Arg Arg Gln Gly Gly
145                 150                 155                 160

Ile Gln Leu Leu Val Asp Leu Leu Asp His Arg Met Thr Glu Val His
                165                 170                 175

Arg Ser Ala Cys Gly Ala Leu Arg Asn Leu Val Tyr Gly Lys Ala Asn
            180                 185                 190

Asp Asp Asn Lys Ile Ala Leu Lys Asn Cys Gly Gly Ile Pro Ala Leu
        195                 200                 205

Val Arg Leu Leu Arg Lys Thr Thr Asp Leu Glu Ile Arg Glu Leu Val
    210                 215                 220

Thr Gly Val Leu Trp Asn Leu Ser Ser Cys Asp Ala Leu Lys Met Pro
225                 230                 235                 240

Ile Ile Gln Asp Ala Leu Ala Val Leu Thr Asn Ala Val Ile Ile Pro
                245                 250                 255

His Ser Gly Trp Glu Asn Ser Pro Leu Gln Asp Asp Arg Lys Ile Gln
            260                 265                 270

Leu His Ser Ser Gln Val Leu Arg Asn Ala Thr Gly Cys Leu Arg Asn
        275                 280                 285

Val Ser Ser Pro Gly Glu Glu Ala Arg Arg Met Arg Glu Cys Asp
    290                 295                 300

Gly Leu Thr Asp Ala Leu Leu Tyr Val Ile Gln Ser Ala Leu Gly Ser
305                 310                 315                 320

Ser Glu Ile Asp Ser Lys Thr Val Glu Asn Cys Val Cys Ile Leu Arg
                325                 330                 335

Asn Leu Ser Tyr Arg Leu Ala Ala Glu Thr Ser Gln Gly Gln His Met
            340                 345                 350

Gly Thr Asp Glu Leu Asp Gly Leu Leu Cys Gly Glu Ala Asn Gly Lys
        355                 360                 365

Asp Ala Glu Ser Ser Gly Cys Trp Gly Lys Lys Lys Lys Lys
    370                 375                 380

Ser Gln Asp Gln Trp Asp Gly Val Gly Pro Leu Pro Asp Cys Ala Glu
385                 390                 395                 400

Pro Pro Lys Gly Ile Gln Met Leu Trp His Pro Ser Ile Val Lys Pro
                405                 410                 415

Tyr Leu Thr Leu Leu Ser Glu Cys Ser Asn Pro Asp Thr Leu Glu Gly
            420                 425                 430

Ala Ala Gly Ala Leu Gln Asn Leu Ala Ala Gly Ser Trp Lys Trp Ser
        435                 440                 445

Val Tyr Ile Arg Ala Ala Val Arg Lys Glu Lys Gly Arg Pro Ile Leu
    450                 455                 460

Val Glu Leu Leu Arg Ile Asp Asn Asp Arg Val Ala Cys Ala Val Ala
465                 470                 475                 480
```

-continued

```
Thr Ala Leu Arg Asn Met Ala Leu Asp Val Arg Asn Lys Glu Leu Ile
                485                 490                 495
Gly Lys Tyr Ala Met Arg Asp Leu Val His Arg Leu Pro Gly Gly Asn
            500                 505                 510
Asn Ser Asn Asn Thr Ala Ser Lys Ala Met Ser Asp Thr Val Thr
        515                 520                 525
Ala Val Cys Cys Thr Leu His Glu Val Ile Thr Lys Asn Met Glu Asn
530                 535                 540
Ala Lys Ala Leu Arg Asp Ala Gly Gly Ile Glu Lys Leu Val Gly Ile
545                 550                 555                 560
Ser Lys Ser Lys Gly Asp Lys His Ser Pro Lys Val Val Lys Ala Ala
                565                 570                 575
Ser Gln Val Leu Asn Ser Met Trp Gln Tyr Arg Asp Leu Arg Ser Leu
            580                 585                 590
Tyr Lys Lys Asp Gly Trp Ser Gln Tyr His Phe Val Ala Ser Ser Ser
        595                 600                 605
Thr Ile Glu Arg Asp Arg Gln Arg Pro Tyr Ser Ser Ser Arg Thr Pro
    610                 615                 620
Ser Ile Ser Pro Val Arg Val Ser Pro Asn Asn Arg Ser Ala Ser Ala
625                 630                 635                 640
Pro Ala Ser Pro Arg Glu Met Ile Ser Leu Lys Glu Arg Lys Thr Asp
                645                 650                 655
Tyr Glu Cys Thr Gly Ser Asn Ala Thr Tyr His Gly Ala Lys Gly Glu
            660                 665                 670
His Thr Ser Arg Lys Asp Ala Met Thr Ala Gln Asn Thr Gly Ile Ser
        675                 680                 685
Thr Leu Tyr Arg Asn Ser Thr Arg Asn Tyr Asp Glu Ser Phe Phe Glu
    690                 695                 700
Asp Gln Val His His Arg Pro Pro Ala Ser Glu Tyr Thr Met His Leu
705                 710                 715                 720
Gly Leu Lys Ser Thr Gly Asn Tyr Val Asp Phe Tyr Ser Ala Ala Arg
                725                 730                 735
Pro Tyr Ser Glu Leu Asn Tyr Glu Thr Ser His Tyr Pro Ala Ser Pro
            740                 745                 750
Asp Ser Trp Val
        755
```

(2) INFORMATION FOR SEQ ID NO: 3:

(i) SEQUENCE CHARACTERISTICS:
        (A) LENGTH: 44 amino acids
        (B) TYPE: amino acid
        (D) TOPOLOGY: linear (ii) MOLECULE TYPE: peptide (ix) FEATURE:
        (B) LOCATION: 11, 13-14, 16-18, 21, 23, 33-36, and 41-44
        (D) OTHER INFORMATION: where Xaa at positions 11, 13-14,
            16-18, 21, 23, 33-36, and 41-44 is any amino acid (xi) SEQUENCE DESCRIPTION: SEQ ID NO: 3:

```
Gly Gly Ile Pro Ala Leu Val Arg Leu Leu Xaa Asn Xaa Xaa Asp Xaa
 1               5                  10                  15
Xaa Xaa Leu Leu Xaa Ala Ala Xaa Gly Val Leu Arg Asn Leu Ser Xaa
            20                  25                  30
Xaa Xaa Xaa Xaa Asn Lys Ala Ile Xaa Xaa Xaa Xaa
        35                  40
```

(2) INFORMATION FOR SEQ ID NO: 4:

(i) SEQUENCE CHARACTERISTICS:
        (A) LENGTH: 44 amino acids
        (B) TYPE: amino acid
        (D) TOPOLOGY: linear (ii) MOLECULE TYPE: peptide (xi) SEQUENCE DESCRIPTION: SEQ ID NO: 4:

```
Gly Gly Ile Gln Leu Leu Val Asp Leu Leu Asp His Arg Met Thr Glu
 1               5                  10                  15

Val His Arg Ser Ala Cys Gly Ala Leu Arg Asn Leu Val Tyr Gly Lys
            20                  25                  30

Ala Asn Asp Asp Asn Lys Ile Ala Leu Lys Asn Cys
            35                  40
```

(2) INFORMATION FOR SEQ ID NO: 5:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO: 5:

```
Gly Gly Ile Pro Ala Leu Val Arg Leu Leu Arg Lys Thr Thr Asp Leu
 1               5                  10                  15

Glu Ile Arg Glu Leu Val Thr Gly Val Leu Trp Asn Leu Ser Ser Cys
            20                  25                  30

Asp Ala Leu Lys Met Pro Ile Ile Gln
            35                  40
```

(2) INFORMATION FOR SEQ ID NO: 6:

(i) SEQUENCE CHARACTERISTICS:
        (A) LENGTH: 39 amino acids
        (B) TYPE: amino acid
        (D) TOPOLOGY: linear (ii) MOLECULE TYPE: peptide (xi) SEQUENCE DESCRIPTION: SEQ ID NO: 6:

```
Ser Ile Val Lys Pro Tyr Leu Thr Leu Leu Ser Glu Cys Ser Asn Pro
 1               5                  10                  15

Asp Thr Leu Glu Gly Ala Ala Gly Ala Leu Gln Asn Leu Ala Ala Gly
            20                  25                  30

Ser Trp Lys Trp Ser Val Tyr
            35
```

(2) INFORMATION FOR SEQ ID NO: 7:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO: 7:

```
Lys Gly Arg Pro Ile Leu Val Glu Leu Leu Arg Ile Asp Asn Asp Arg
 1               5                  10                  15
```

-continued

```
Val Ala Cys Ala Val Ala Thr Ala Leu Arg Asn Met Ala Leu Asp Val
            20                  25                  30

Arg Asn Lys Glu Leu Ile Gly Lys Tyr
            35                  40

(2) INFORMATION FOR SEQ ID NO: 8:

(i) SEQUENCE CHARACTERISTICS:
        (A) LENGTH: 686 amino acids
        (B) TYPE: amino acid
        (D) TOPOLOGY: linear (ii) MOLECULE TYPE: protein (xi) SEQUENCE DESCRIPTION: SEQ ID NO: 8:

Ser Gln Ser Gln Gly Val Pro Leu Pro Pro Ala His Thr Gly Thr Tyr
  1               5                  10                  15

Arg Thr Ser Thr Ala Pro Ser Ser Pro Gly Val Asp Ser Val Pro Leu
             20                  25                  30

Gln Arg Thr Gly Ser Gln His Gly Pro Gln Asn Ala Ala Ala Ala Thr
             35                  40                  45

Phe Gln Arg Ala Ser Tyr Ala Ala Gly Pro Ala Ser Asn Tyr Ala Asp
 50                      55                  60

Pro Tyr Arg Gln Leu Gln Tyr Cys Pro Ser Val Glu Ser Pro Tyr Ser
 65                  70                  75                  80

Lys Ser Gly Pro Ala Leu Pro Pro Glu Gly Thr Leu Ala Arg Ser Pro
                 85                  90                  95

Ser Ile Asp Ser Ile Gln Lys Asp Pro Arg Glu Phe Gly Trp Arg Asp
                100                 105                 110

Pro Glu Leu Pro Glu Val Ile Gln Met Leu Gln His Gln Phe Pro Ser
            115                 120                 125

Val Gln Ser Asn Ala Ala Tyr Leu Gln His Leu Cys Phe Gly Asp
            130                 135                 140

Asn Lys Ile Lys Ala Glu Ile Arg Arg Gln Gly Gly Ile Gln Leu Leu
145                 150                 155                 160

Val Asp Leu Leu Asp His Arg Met Thr Glu Val His Arg Ser Ala Cys
                165                 170                 175

Gly Ala Leu Arg Asn Leu Val Tyr Gly Lys Ala Asn Asp Asp Asn Lys
            180                 185                 190

Ile Ala Leu Lys Asn Cys Gly Gly Ile Pro Ala Leu Val Arg Leu Leu
            195                 200                 205

Arg Lys Thr Thr Asp Leu Glu Ile Arg Glu Leu Val Thr Gly Val Leu
            210                 215                 220

Trp Asn Leu Ser Ser Cys Asp Ala Leu Lys Met Pro Ile Ile Gln Asp
225                 230                 235                 240

Ala Leu Ala Val Leu Thr Asn Ala Val Ile Ile Pro His Ser Gly Trp
                245                 250                 255

Glu Asn Ser Pro Leu Gln Asp Asp Arg Lys Ile Gln Leu His Ser Ser
            260                 265                 270

Gln Val Leu Arg Asn Ala Thr Gly Cys Leu Arg Asn Val Ser Ser Pro
            275                 280                 285

Gly Glu Glu Ala Arg Arg Arg Met Arg Glu Cys Asp Gly Leu Thr Asp
            290                 295                 300

Ala Leu Leu Tyr Val Ile Gln Ser Ala Leu Gly Ser Ser Glu Ile Asp
305                 310                 315                 320

Ser Lys Thr Val Glu Asn Cys Val Cys Ile Leu Arg Asn Leu Ser Tyr
```

-continued

```
                325                 330                 335
Arg Leu Ala Ala Glu Thr Ser Gln Gly Gln His Met Gly Thr Asp Glu
                340                 345                 350
Leu Asp Gly Leu Leu Cys Gly Glu Ala Asn Gly Lys Asp Ala Glu Ser
                355                 360                 365
Ser Gly Cys Trp Gly Lys Lys Lys Lys Lys Lys Ser Gln Asp Gln
                370                 375                 380
Trp Asp Gly Val Gly Pro Leu Pro Asp Cys Ala Glu Pro Pro Lys Gly
385                 390                 395                 400
Ile Gln Met Leu Trp His Pro Ser Ile Val Lys Pro Tyr Leu Thr Leu
                405                 410                 415
Leu Ser Glu Cys Ser Asn Pro Asp Thr Leu Glu Gly Ala Ala Gly Ala
                420                 425                 430
Leu Gln Asn Leu Ala Ala Gly Ser Trp Lys Trp Ser Val Tyr Ile Arg
                435                 440                 445
Ala Ala Val Arg Lys Glu Lys Gly Arg Pro Ile Leu Val Glu Leu Leu
                450                 455                 460
Arg Ile Asp Asn Asp Arg Val Ala Cys Ala Val Ala Thr Ala Leu Arg
465                 470                 475                 480
Asn Met Ala Leu Asp Val Arg Asn Lys Glu Leu Ile Gly Lys Tyr Ala
                485                 490                 495
Met Arg Asp Leu Val His Arg Leu Pro Gly Gly Asn Ser Asn Asn
                500                 505                 510
Thr Ala Ser Lys Ala Met Ser Asp Asp Thr Val Thr Ala Val Cys Cys
                515                 520                 525
Thr Leu His Glu Val Ile Thr Lys Asn Met Glu Asn Ala Lys Ala Leu
                530                 535                 540
Arg Asp Ala Gly Gly Ile Glu Lys Leu Val Gly Ile Ser Lys Ser Lys
545                 550                 555                 560
Gly Asp Lys His Ser Pro Lys Val Val Lys Ala Ala Ser Gln Val Leu
                565                 570                 575
Asn Ser Met Trp Gln Tyr Arg Asp Leu Arg Ser Leu Tyr Lys Lys Asp
                580                 585                 590
Gly Trp Ser Gln Tyr His Phe Val Ala Ser Ser Thr Ile Glu Arg
                595                 600                 605
Asp Arg Gln Arg Pro Tyr Ser Ser Arg Thr Pro Ser Ile Ser Pro
                610                 615                 620
Val Arg Val Ser Pro Asn Asn Arg Ser Ala Ser Ala Pro Ala Ser Pro
625                 630                 635                 640
Arg Glu Met Ile Ser Leu Lys Glu Arg Lys Thr Asp Tyr Glu Cys Thr
                645                 650                 655
Gly Ser Asn Ala Thr Tyr His Gly Ala Lys Gly Glu His Thr Ser Arg
                660                 665                 670
Lys Asp Ala Met Thr Ala Gln Asn Thr Gly Ile Ser Thr Leu
                675                 680                 685
```

(2) INFORMATION FOR SEQ ID NO: 9:

(i) SEQUENCE CHARACTERISTICS:
      (A) LENGTH: 682 amino acids
      (B) TYPE: amino acid
      (D) TOPOLOGY: linear (ii) MOLECULE TYPE: protein (xi) SEQUENCE DESCRIPTION: SEQ ID NO: 9:

-continued

```
Ser Leu Ser Arg Val Thr Arg Ile Glu Glu Arg Tyr Arg Pro Ser Met
  1               5                  10                  15

Gln Val Arg Val Gly Gly Ser Ser Val Asp Leu His Arg Phe His Pro
             20                  25                  30

Gln Val Arg Val Gly Gly Ser Ser Val Asp Leu His Arg Phe His Pro
             35                  40                  45

Glu Pro Tyr Gly Leu Glu Asp Asp Gln Arg Ser Met Gly Tyr Asp Asp
     50                  55                  60

Leu Asp Tyr Gly Met Met Ser Asp Tyr Gly Thr Ala Arg Arg Thr Gly
 65              70                  75                  80

Thr Pro Ser Asp Pro Arg Arg Leu Arg Ser Thr Glu Asp Met Ile
                 85                  90                  95

Gly Glu Glu Val Pro Pro Asp Gln Tyr Tyr Trp Ala Pro Leu Ala Gln
            100                 105                 110

His Glu Arg Gly Ser Leu Ala Ser Leu Asp Ser Leu Arg Lys Gly Met
            115                 120                 125

Pro Pro Pro Ser Asn Trp Arg Gln Pro Glu Leu Pro Glu Val Ile Ala
130                 135                 140

Met Leu Gly Phe Arg Leu Asp Ala Val Lys Ser Asn Ala Ala Ala Tyr
145                 150                 155                 160

Leu Gln His Leu Cys Tyr Arg Asn Asp Lys Val Lys Thr Asp Val Ala
                165                 170                 175

Lys Leu Lys Gly Ile Pro Ile Leu Val Gly Leu Leu Asp His Pro Lys
                180                 185                 190

Lys Glu Val His Leu Gly Ala Cys Gly Ala Leu Lys Asn Ile Ser Phe
                195                 200                 205

Gly Arg Asp Gln Asp Asn Lys Ile Ala Ile Lys Asn Cys Asp Gly Val
            210                 215                 220

Pro Ala Leu Val Arg Leu Leu Arg Lys Ala Arg Asp Met Asp Leu Thr
225                 230                 235                 240

Glu Val Ile Thr Gly Thr Leu Trp Asn Leu Ser Ser His Asp Ser Ile
                245                 250                 255

Lys Met Glu Ile Val Asp His Ala Leu His Ala Leu Thr Asp Glu Val
                260                 265                 270

Ile Ile Pro His Ser Gly Trp Glu Arg Glu Pro Asn Glu Asp Cys Lys
                275                 280                 285

Pro Arg His Ile Glu Trp Glu Ser Val Leu Thr Asn Thr Ala Gly Cys
            290                 295                 300

Leu Arg Asn Val Ser Ser Glu Arg Ser Glu Ala Arg Arg Lys Leu Arg
305                 310                 315                 320

Glu Cys Asp Gly Leu Val Asp Ala Leu Ile Phe Ile Val Gln Ala Glu
                325                 330                 335

Ile Gly Gln Lys Asp Ser Asp Ser Lys Leu Val Glu Asn Cys Val Cys
            340                 345                 350

Leu Leu Arg Asn Leu Ser Tyr Gln Val His Arg Glu Ile Pro Gln Ala
            355                 360                 365

Glu Arg Tyr Gln Glu Ala Leu Pro Thr Val Ala Asn Ser Thr Gly Pro
370                 375                 380

His Ala Ala Ser Cys Phe Gly Ala Lys Lys Gly Lys Gly Lys Lys Pro
385                 390                 395                 400

Thr Glu Asp Pro Ala Asn Asp Thr Val Asp Phe Pro Lys Arg Thr Ser
                405                 410                 415
```

```
Pro Ala Arg Gly Tyr Glu Leu Leu Phe Gln Pro Glu Val Val Arg Ile
            420                 425                 430

Tyr Ile Ser Leu Leu Lys Glu Ser Asn Thr Pro Ala Ile Leu Glu Ala
                435                 440                 445

Ser Ala Gly Ala Ile Gln Asn Leu Cys Ala Gly Arg Trp Thr Tyr Gly
450                 455                 460

Arg Tyr Ile Arg Ser Ala Leu Arg Gln Glu Lys Ala Leu Ser Ala Arg
465                 470                 475                 480

Ala Glu Leu Leu Thr Ser Gln His Glu Arg Val Val Lys Ala Ala Ser
                485                 490                 495

Gly Ala Leu Arg Asn Leu Ala Val Asp Ala Arg Asn Lys Glu Leu Ile
            500                 505                 510

Gly Lys His Ala Arg Pro Asn Leu Val Lys Asn Leu Pro Gly Gly Gln
            515                 520                 525

Gln Asn Ser Ser Trp Asn Phe Ser Glu Asp Thr Val Val Ser Ile Leu
            530                 535                 540

Asn Thr Ile Asn Glu Val Ile Ala Glu Asn Leu Glu Ala Ala Lys Lys
545                 550                 555                 560

Leu Arg Glu Thr Gln Gly Ile Glu Lys Leu Val Leu Ile Asn Lys Ser
                565                 570                 575

Gly Asn Arg Ser Glu Lys Glu Val Arg Ala Ala Ala Leu Val Leu Gln
            580                 585                 590

Thr Ile Trp Gly Tyr Lys Glu Leu Arg Lys Pro Leu Glu Lys Glu Gly
            595                 600                 605

Trp Lys Lys Ser Asp Phe Gln Val Asn Leu Asn Asn Ala Ser Arg Ser
            610                 615                 620

Gln Ser Ser His Ser Tyr Asp Asp Ser Thr Leu Pro Leu Ile Asp Arg
625                 630                 635                 640

Asn Gln Lys Ser Asp Asn Asn Tyr Ser Thr Leu Asn Glu Arg Gly Asp
                645                 650                 655

His Asn Arg Thr Leu Asp Arg Ser Gly Asp Leu Gly Asp Met Glu Pro
            660                 665                 670

Leu Lys Gly Ala Pro Leu Met Gln Lys Ile
            675                 680

(2) INFORMATION FOR SEQ ID NO: 10:

(i) SEQUENCE CHARACTERISTICS:
        (A) LENGTH: 620 amino acids
        (B) TYPE: amino acid
        (D) TOPOLOGY: linear (ii) MOLECULE TYPE: protein (xi) SEQUENCE DESCRIPTION: SEQ ID NO: 10:

Arg Ser Leu Ser Gln Ser Gln Gly Val Pro Leu Pro Ala His Thr
1               5                   10                  15

Gly Thr Tyr Arg Thr Ser Thr Ala Pro Ser Ser Pro Gly Val Asp Ser
                20                  25                  30

Val Asp Leu Gln Arg Thr Cys Ser Gln His Cys Ile Gln Asn Ala Ala
            35                  40                  45

Ala Ala Thr Phe Gln Arg Ala Cys Tyr Ala Ala Gly Pro Ala Cys Asn
        50                  55                  60

Tyr Ala Asp Pro Tyr Arg Gln Leu Gln Tyr Cys Pro Ser Val Glu Ser
65                  70                  75                  80

Pro Tyr Ser Lys Ser Gly Pro Ala Leu Pro Pro Glu Gly Thr Leu Ala
```

-continued

```
                85                  90                  95
Arg Ser Pro Ser Ile Asp Ser Ile Gln Lys Asp Phe Arg Glu Phe Gly
                   100                 105                 110
Trp Arg Asp Pro Glu Leu Pro Glu Val Ile Gln Met Leu Gln Met Gln
                   115                 120                 125
Phe Pro Ser Val Gln Ser Asn Ala Ala Ala Tyr Leu Gln His Leu Cys
                   130                 135                 140
Phe Gly Asp Asn Lys Ile Lys Ala Glu Ile Arg Arg Gln Gly Gly Ile
145                 150                 155                 160
Gln Leu Leu Val Asp Leu Leu Asp His Arg Met Thr Arg Val His Arg
                   165                 170                 175
Ser Ala Cys Gly Ala Leu Arg Asn Leu Val Tyr Gly Lys Ala Asn Asp
                   180                 185                 190
Asp Asn Lys Ile Ala Leu Lys Asn Cys Gly Gly Ile Pro Ala Leu Val
                   195                 200                 205
Arg Leu Leu Arg Lys Thr Thr Asp Glu Ile Arg Glu Leu Val Thr
                   210                 215                 220
Gly Val Leu Trp Asn Leu Ser Ser Cys Asp Ala Leu Lys Met Pro Thr
225                 230                 235                 240
Thr Gln Asp Ala Leu Ala Val Leu Thr Asn Ala Val Ile Ile Pro His
                   245                 250                 255
Ser Gly Trp Glu Asn Ser Pro Leu Gln Asp Asp Arg Lys Ile Gln Leu
                   260                 265                 270
His Ser Ser Gln Val Leu Arg Asn Ala Thr Gly Cys Leu Arg Asn Val
                   275                 280                 285
Ser Ser Pro Gly Glu Glu Ala Arg Arg Arg Met Arg Glu Cys Asp Gly
                   290                 295                 300
Leu Thr Asp Ala Leu Leu Tyr Val Ile Gln Ser Ala Leu Gly Ser Ser
305                 310                 315                 320
Glu Ile Asp Ser Lys Thr Val Glu Asn Cys Val Cys Ile Leu Arg Asn
                   325                 330                 335
Leu Ser Tyr Arg Leu Ala Ala Glu Thr Ser Gln Gly Gln His Met Gly
                   340                 345                 350
Thr Asp Glu Leu Asp Gly Leu Leu Cys Cys Glu Ala Asn Cys Phe Asp
                   355                 360                 365
Ala Glu Ser Ser Cys Cys Trp Cys Lys Lys Lys Lys Lys Lys Ser
                   370                 375                 380
Gln Asn Gln Trp Asp Gly Val Gly Pro Leu Pro Asp Cys Ala Glu Pro
385                 390                 395                 400
Pro Lys Gly Ile Gln Met Leu Trp His Pro Ser Ile Val Lys Pro Tyr
                   405                 410                 415
Leu Thr Leu Leu Ser Glu Cys Ser Asn Pro Asp Thr Leu Glu Cys Ala
                   420                 425                 430
Ala Cys Ala Leu Gln Asn Leu Ala Ala Cys Glu Trp Lys Trp Glu Val
                   435                 440                 445
Tyr Ile Arg Ala Ala Val Arg Lys Glu Lys Gly Arg Pro Ile Leu Val
                   450                 455                 460
Glu Leu Leu Arg Ile Asp Asn Asp Arg Val Ala Cys Ala Val Ala Thr
465                 470                 475                 480
Ala Leu Arg Asn Met Ala Leu Asp Val Arg Asn Lys Glu Leu Ile Gly
                   485                 490                 495
Lys Tyr Ala Met Arg Asp Leu Val His Arg Leu Pro Gly Gly Asn Asn
                   500                 505                 510
```

-continued

```
Ser Asn Asn Thr Ala Ser Lys Ala Met Ser Asp Asp Thr Val Thr Ala
            515                 520                 525

Val Cys Cys Thr Leu His Glu Val Ile Thr Lys Asn Met Glu Asn Ala
        530                 535                 540

Lys Ala Leu Arg Asp Ala Gly Gly Ile Glu Lys Leu Val Gly Ile Ser
545                 550                 555                 560

Lys Ser Lys Gly Asp Lys His Ser Pro Lys Val Val Lys Ala Ala Ser
                565                 570                 575

Gln Val Leu Asn Ser Met Trp Gln Tyr Arg Asp Leu Arg Ser Leu Tyr
            580                 585                 590

Lys Lys Asp Gly Trp Ser Gln Tyr His Phe Val Ala Ser Ser Ser Thr
            595                 600                 605

Ile Glu Arg Asp Arg Gln Arg Pro Tyr Arg Arg Arg
610                 615                 620

(2) INFORMATION FOR SEQ ID NO: 11:

(i) SEQUENCE CHARACTERISTICS:
        (A) LENGTH: 666 amino acids
        (B) TYPE: amino acid
        (D) TOPOLOGY: linear (ii) MOLECULE TYPE: protein (xi) SEQUENCE DESCRIPTION: SEQ ID NO: 11:

Ser Thr Leu Ser Met Ser Asn Arg Gly Ser Met Tyr Asp Gly Leu Ala
1               5                   10                  15

Asp Asn Tyr Asn Tyr Gly Thr Thr Ser Lys Ser Ser Tyr Tyr Ser Lys
            20                  25                  30

Phe Gln Ala Gly Asn Gly Ser Trp Gly Tyr Pro Ile Tyr Asn Gly Thr
        35                  40                  45

Leu Lys Arg Glu Pro Asp Asn Arg Arg Phe Ser Ser Tyr Ser Gln Met
    50                  55                  60

Glu Asn Trp Arg Arg His Tyr Pro Arg Gly Ser Cys Asn Thr Thr Gly
65                  70                  75                  80

Ala Gly Ser Asp Ile Cys Phe Met Gln Lys Ile Lys Ala Ser Arg Ser
                85                  90                  95

Ile Asp Asp Leu Tyr Cys Asp Pro Arg Gly Thr Leu Arg Lys Gly Thr
                100                 105                 110

Leu Gly Ser Lys Gly Gln Lys Thr Thr Gln Met Arg Tyr Ser Phe Tyr
            115                 120                 125

Ser Thr Cys Ser Gly Gln Lys Ala Ile Lys Lys Cys Pro Val Arg Pro
130                 135                 140

Pro Ser Cys Ala Ser Lys Gln Asp Pro Val Tyr Ile Pro Pro Ile Ser
145                 150                 155                 160

Cys Asn Lys Asp Leu Ser Phe Gly Trp Ser Arg Ala Ser Ser Lys Ile
                165                 170                 175

Cys Ser Glu Asp Ile Glu Cys Ser Cys Leu Thr Ile Pro Lys Ala Val
            180                 185                 190

Gln Tyr Leu Glu Glu Gln Asp Glu Lys Tyr Gln Ala Ile Gly Ala Tyr
        195                 200                 205

Tyr Ile Gln His Thr Cys Phe Gln Asp Glu Ser Ala Lys Gln Gln Val
            210                 215                 220

Tyr Gln Leu Gly Gly Ile Cys Lys Leu Val Asp Leu Leu Arg Ser Pro
225                 230                 235                 240
```

```
Asn Gln Asn Val Gln Gln Ala Ala Ala Cys Ala Leu Arg Asn Leu Val
                245                 250                 255
Phe Arg Glu Thr Thr Asn Lys Leu Glu Thr Arg Arg Gln Asn Gly Ile
                260                 265                 270
Arg Glu Ala Val Glu Leu Leu Arg Arg Thr Gly Asn Ala Glu Ile Gln
                275                 280                 285
Lys Gln Leu Thr Gly Leu Leu Trp Asn Leu Ser Ser Thr Asp Glu Leu
                290                 295                 300
Lys Glu Glu Leu Ile Ala Asp Ala Leu Pro Val Leu Ala Asp Arg Val
305                 310                 315                 320
Ile Ile Pro Phe Ser Gly Trp Cys Asp Gly Asn Ser Asn Met Ser Arg
                325                 330                 335
Glu Val Val Asp Pro Glu Val Phe Phe Asn Ala Thr Gly Cys Leu Arg
                340                 345                 350
Asn Leu Ser Ser Ala Asp Ala Gly Arg Gln Thr Met Arg Asn Tyr Ser
                355                 360                 365
Gly Leu Ile Asp Ser Leu Met Ala Tyr Val Gln Met Cys Val Ala Ala
                370                 375                 380
Ser Arg Cys Asp Asp Lys Ser Val Glu Asn Cys Met Cys Val Leu His
385                 390                 395                 400
Asn Leu Ser Tyr Arg Leu Asp Ala Glu Val Pro Thr Arg Tyr Arg Gln
                405                 410                 415
Leu Glu Tyr Asn Ala Arg Asn Ala Tyr Thr Glu Lys Ser Ser Thr Gly
                420                 425                 430
Cys Glu Ser Asn Lys Ser Asp Lys Met Met Asn Asn Asn Tyr Asp Cys
                435                 440                 445
Pro Leu Pro Glu Glu Glu Ile Asn Pro Lys Gly Ser Gly Trp Leu Tyr
                450                 455                 460
His Ser Asp Ala Ile Arg Thr Tyr Leu Asn Leu Met Gly Lys Ser Lys
465                 470                 475                 480
Lys Asp Ala Thr Leu Glu Ala Cys Ala Gly Ala Leu Gln Asn Thr Thr
                485                 490                 495
Ala Ser Lys Gly Leu Met Ser Ser Gly Met Ser Gln Leu Ile Gly Leu
                500                 505                 510
Lys Glu Lys Gly Leu Pro Gln Ile Ala Arg Leu Leu Gln Ser Gly Asn
                515                 520                 525
Ser Asp Val Val Arg Ser Gly Ala Ser Leu Leu Ser Asn Met Ser Lys
                530                 535                 540
Lys Pro Leu Leu Met Lys Val Met Gly Asn Gln Val Phe Pro Glu Val
545                 550                 555                 560
Thr Arg Leu Leu Thr Ser His Thr Gly Asn Thr Ser Asn Ser Glu Asp
                565                 570                 575
Ile Leu Ser Ser Ala Cys Tyr Thr Val Arg Asn Leu Met Ala Ser Gln
                580                 585                 590
Pro Gln Leu Ala Lys Gln Tyr Phe Ser Ser Met Leu Asn Asn Ile
                595                 600                 605
Ile Asn Leu Cys Arg Ser Ser Ala Ser Pro Lys Ala Ala Glu Ala Ala
                610                 615                 620
Arg Leu Leu Leu Ser Asp Met Trp Ser Ser Lys Glu Leu Gln Gly Val
625                 630                 635                 640
Leu Arg Gln Gln Gly Phe Asp Arg Asn Met Leu Gly Thr Leu Ala Gly
                645                 650                 655
Ala Asn Ser Leu Arg Asn Phe Thr Ser Arg
```

```
                    660             665
```

(2) INFORMATION FOR SEQ ID NO: 12:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 12:

```
Gly Asn Ile Lys Ser Tyr Phe Arg Lys Leu Asn Glu Ser Gln Val
 1               5                  10                  15
```

(2) INFORMATION FOR SEQ ID NO: 13:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO: 13:

```
Tyr Glu Thr Ser His Tyr Pro Ala Ser Pro Asp Ser Trp Val
 1               5                  10
```